US012456344B2

(12) United States Patent
Urban et al.

(10) Patent No.: US 12,456,344 B2
(45) Date of Patent: Oct. 28, 2025

(54) ADJUSTABLE ELECTRONIC GAMING DEVICE AND ASSOCIATED SYSTEMS AND METHODS

(71) Applicant: Aristocrat Technologies, Inc., Las Vegas, NV (US)

(72) Inventors: Bruce Urban, Las Vegas, NV (US); Ariel Turgel, San Francisco, CA (US); Daniel Harden, Palo Alto, CA (US); Craig Paulsen, Reno, NV (US)

(73) Assignee: Aristocrat Technologies, Inc., Las Vegas, NV (US)

( * ) Notice: Subject to any disclaimer, the term of this patent is extended or adjusted under 35 U.S.C. 154(b) by 378 days.

(21) Appl. No.: 18/160,174

(22) Filed: Jan. 26, 2023

(65) Prior Publication Data

US 2023/0267801 A1 Aug. 24, 2023

Related U.S. Application Data

(60) Provisional application No. 63/311,815, filed on Feb. 18, 2022.

(51) Int. Cl.
*G07F 17/32* (2006.01)
*A61L 2/24* (2006.01)

(52) U.S. Cl.
CPC ............ *G07F 17/3216* (2013.01); *A61L 2/24* (2013.01); *G07F 17/3209* (2013.01); *G07F 17/3213* (2013.01)

(58) Field of Classification Search
CPC ............. G07F 17/3209; G07F 17/3211; G07F 17/3213; G07F 17/3216
See application file for complete search history.

(56) References Cited

U.S. PATENT DOCUMENTS

| | | | | |
|---|---|---|---|---|
| 6,514,145 | B1 | 2/2003 | Kawabata | |
| 7,673,879 | B2 * | 3/2010 | Collings | G07F 17/32 463/47 |
| 8,974,297 | B2 * | 3/2015 | Massing | G07F 17/3216 463/31 |
| 9,711,001 | B2 * | 7/2017 | Zedell, Jr. | G07F 17/3241 |
| 10,607,438 | B2 | 3/2020 | Froy | |
| 10,850,184 | B1 | 12/2020 | Colvin | |
| 10,872,490 | B2 | 12/2020 | Winston | |
| 10,946,110 | B1 | 3/2021 | Colvin | |
| 11,097,024 | B1 | 8/2021 | Colvin | |
| 11,097,025 | B1 | 8/2021 | Colvin | |
| 11,344,791 | B2 | 5/2022 | Colvin | |
| 11,471,751 | B2 | 10/2022 | Colvin | |
| 11,491,250 | B2 | 11/2022 | Colvin | |

(Continued)

FOREIGN PATENT DOCUMENTS

EP 1074954 B1 9/2010

*Primary Examiner* — Milap Shah
(74) *Attorney, Agent, or Firm* — Armstrong Teasdale LLP

(57) ABSTRACT

An electronic gaming device is described. The electronic gaming device includes a display device, a base, and a moveable coupling mechanism configured to couple the display device to the base and facilitate movement of the display device along an arcuate path and relative to the base between a first position and a second position wherein in the first position the display device is held in an upright position and in the second position the display device is held in a lowered position.

20 Claims, 11 Drawing Sheets

(56) References Cited

U.S. PATENT DOCUMENTS

| | | | | |
|---|---|---|---|---|
| 2004/0004049 | A1* | 1/2004 | Geiger | G07F 17/32 211/49.1 |
| 2004/0012146 | A1* | 1/2004 | Luciano, Jr. | G07F 17/32 273/148 R |
| 2006/0183544 | A1* | 8/2006 | Okada | G07F 17/3216 463/31 |
| 2006/0199648 | A1* | 9/2006 | Mitchell | G07F 17/3216 463/47 |
| 2008/0070701 | A1* | 3/2008 | Mou | G07F 17/34 463/46 |
| 2008/0116342 | A1* | 5/2008 | Oliver | A47G 23/0225 248/311.2 |
| 2009/0233681 | A1 | 9/2009 | Tsukahara | |
| 2012/0004030 | A1* | 1/2012 | Kelly | G07F 17/34 463/31 |
| 2012/0122569 | A1* | 5/2012 | Kowolik | G07F 17/3211 463/30 |
| 2012/0220363 | A1* | 8/2012 | Bytnar | G07F 17/3216 463/25 |
| 2018/0053373 | A1* | 2/2018 | Goldstein | G07F 17/3213 |
| 2018/0276942 | A1* | 9/2018 | Whelan | G07F 17/3227 |
| 2020/0035061 | A1* | 1/2020 | Froy | G07F 17/3213 |
| 2020/0111299 | A1* | 4/2020 | Baker | G07F 17/3223 |
| 2020/0388106 | A1* | 12/2020 | Urban | G07F 17/3216 |
| 2021/0090382 | A1* | 3/2021 | McNierney | G07F 17/3216 |
| 2021/0095505 | A1* | 4/2021 | Chaudhari | G07F 17/3216 |
| 2021/0322588 | A1 | 10/2021 | Colvin | |
| 2021/0322603 | A1 | 10/2021 | Colvin | |
| 2022/0176230 | A1 | 6/2022 | Colvin | |
| 2023/0267801 | A1* | 8/2023 | Urban | G07F 17/3209 463/46 |

* cited by examiner

ADJUSTABLE ELECTRONIC GAMING DEVICE AND ASSOCIATED SYSTEMS AND METHODS

CROSS REFERENCE TO RELATED APPLICATIONS

This application claims the benefit of priority to U.S. Provisional Patent Application No. 63/311,815, filed Feb. 18, 2022, which is incorporated herein by reference in its entirety.

TECHNICAL FIELD

This application is directed to electronic gaming, and more specifically to an adjustable electronic gaming device and associated systems and methods.

BACKGROUND

Electronic gaming machines ("EGMs") or gaming devices provide a variety of wagering games such as slot games, video poker games, video blackjack games, roulette games, video bingo games, keno games and other types of games that are frequently offered at casinos and other locations. Play on EGMs typically involves a player establishing a credit balance by inputting money, or another form of monetary credit, and placing a monetary wager (from the credit balance) on one or more outcomes of an instance (or single play) of a primary or base game. In some cases, a player may qualify for a special mode of the base game, a secondary game, or a bonus round of the base game by attaining a certain winning combination or triggering event in, or related to, the base game, or after the player is randomly awarded the special mode, secondary game, or bonus round. In the special mode, secondary game, or bonus round, the player is given an opportunity to win extra game credits, game tokens or other forms of payout. In the case of "game credits" that are awarded during play, the game credits are typically added to a credit meter total on the EGM and can be provided to the player upon completion of a gaming session or when the player wants to "cash out."

"Slot" type games are often displayed to the player in the form of various symbols arrayed in a row-by-column grid or matrix. Specific matching combinations of symbols along predetermined paths (or paylines) through the matrix indicate the outcome of the game. The display typically highlights winning combinations/outcomes for identification by the player. Matching combinations and their corresponding awards are usually shown in a "pay-table" which is available to the player for reference. Often, the player may vary his/her wager to include differing numbers of paylines and/or the amount bet on each line. By varying the wager, the player may sometimes alter the frequency or number of winning combinations, frequency or number of secondary games, and/or the amount awarded.

Typical games use a random number generator (RNG) to randomly determine the outcome of each game. The game is designed to return a certain percentage of the amount wagered back to the player over the course of many plays or instances of the game, which is generally referred to as return to player (RTP). The RTP and randomness of the RNG ensure the fairness of the games and are highly regulated. Upon initiation of play, the RNG randomly determines a game outcome and symbols are then selected which correspond to that outcome. Notably, some games may include an element of skill on the part of the player and are therefore not entirely random.

BRIEF DESCRIPTION

In one aspect, an electronic gaming device is described. The electronic gaming device includes a display device, a base, and a moveable coupling mechanism configured to couple the display device to the base and facilitate movement of the display device along an arcuate path and relative to the base between a first position and a second position wherein in the first position the display device is held in an upright position and in the second position the display device is held in a lowered position.

In another aspect, an electronic gaming system is described. The electronic gaming system includes a display device, a base, and a moveable coupling mechanism configured to couple the display device to the base and facilitate movement of the display device along an arcuate path and relative to the base between a first position and a second position wherein in the first position the display device is held in an upright position and in the second position the display device is held in a lowered position.

In another aspect, a method for configuring a display device of an electronic gaming device to be moveable between a first position and a second position is described. The method includes coupling a base to a moveable coupling mechanism and coupling the display device to the moveable coupling mechanism wherein the moveable coupling mechanism is configured to facilitate movement of the display device along an arcuate path and relative to the base between the first position and the second position and wherein in the first position the display device is held in an upright position and in the second position the display device is held in a lowered position.

DETAILED DESCRIPTION

Figure 1:
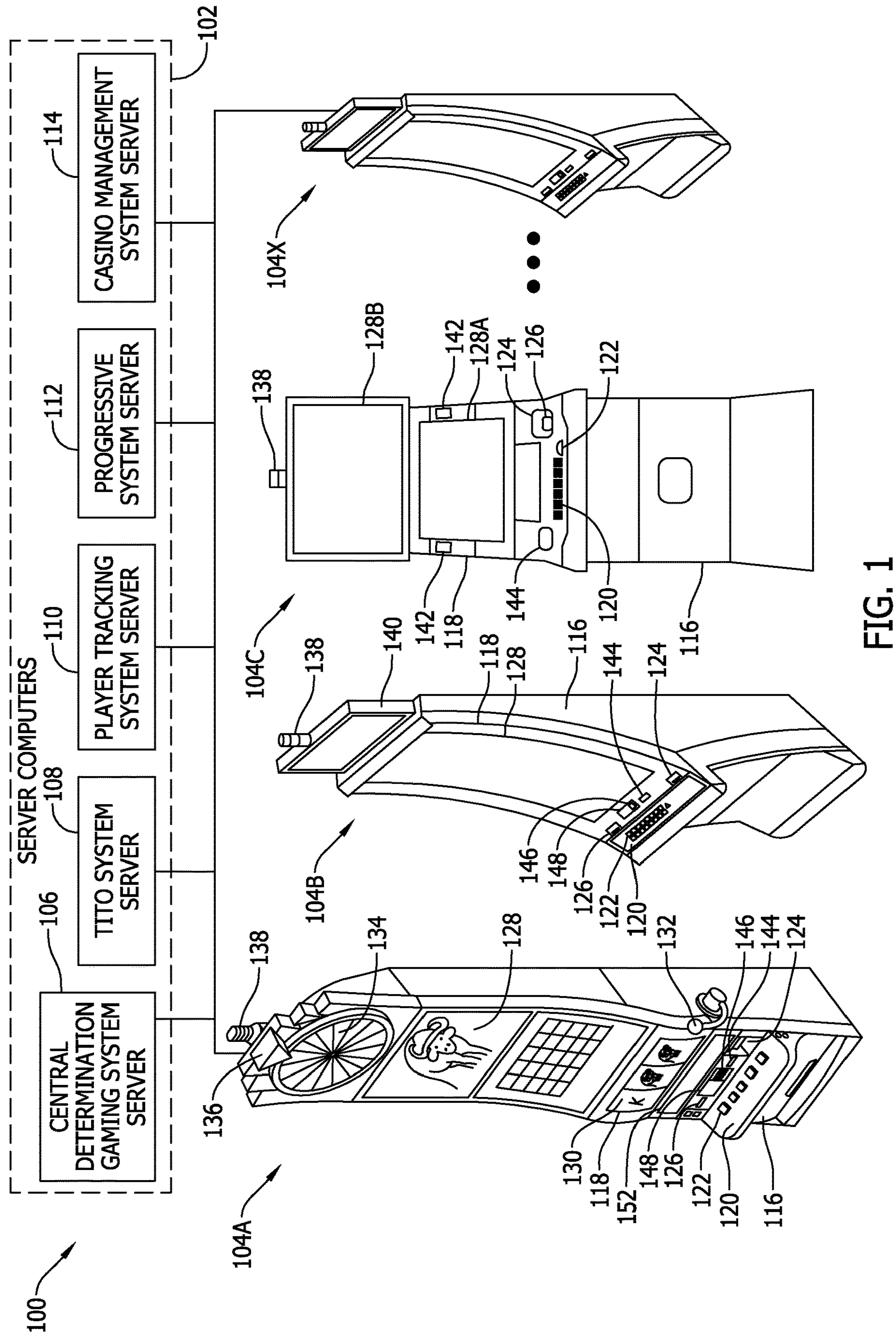
FIG. 1 is an exemplary diagram showing several EGMs networked with various gaming related servers.

An adjustable gaming device is described herein. In the example embodiment, the adjustable gaming device or portion thereof is adjustable between a first position and a second position and a plurality of positions therebetween. In some embodiments, the first position may be a substantially upright/vertical position while the second position may be a substantially slanted position. The device may also be adjusted to another position of the plurality of positions between the first and second positions. For example, the substantially upright/vertical position may be desirable for some players playing while standing at the adjustable gaming device, while the substantially slanted position may be desirable for players playing while hunched over or seated at the adjustable gaming device. Traditional gaming devices do not offer the customization of, control of, and flexibility of the example adjustable gaming device described herein.

A display device of the adjustable gaming device may be coupled to a base of the adjustable gaming device by an adjustable coupling mechanism configured to facilitate movement of the display device between the first position and the second position. As an example, the adjustable coupling mechanism may include a gearing system including a pinion/barrel that rolls along a track (e.g., rails) to control movement of the display device. In some embodiments, the gearing system includes a motor that controls movement of the pinion (e.g., in response to an input, for example at a button of the adjustable gaming device). In some embodiments, the gearing system includes no motor (e.g., movement of the display device may be controlled manually by a user (e.g., a player, a technician, etc.) applying force to the display device or gearing system). In some embodiments, the gearing system includes a release mechanism configured to lock and/or unlock the gearing system. For example, when the release is locked, the gearing system does not allow movement of the display device. When the release is unlocked, the gearing system allows movement of the display device (e.g., similar to the lever of an office chair that locks/unlocks to control chair height).

In some embodiments, the adjustable gaming device is configured to automatically move between the first position, the second position, or any position therebetween. For example, a player may input a player tracking card (or any identifying input, such as connecting a mobile device) to the adjustable gaming device. A lookup may then be performed (e.g., by the adjustable gaming device or a backend server in communication with the adjustable gaming device) to identify a player account associated with the player and preferences included in the player account, such as a desired position of a display device of the adjustable gaming device. The display device may then automatically be caused to move to the desired position (e.g., a favorite position stored in the player account).

In some embodiments, the player preferences, such as a preferred position of the display device, may be received from a mobile device of a player. In some embodiments, a control panel (e.g., including virtual buttons) may be displayed on the mobile device of the player (e.g., when the mobile device is connected to the adjustable gaming device). Inputs at the control panel may then remotely cause the display device to move between the first position and the second position (e.g., selection of a "+" button may cause the display device to move toward the first position while selection of a "−" button may cause the display device to move toward the second position). In some embodiments, the control panel may be provided on the display device of the adjustable gaming device or any other device in communication with the adjustable gaming device.

In the example embodiment, the adjustable gaming device includes at least one peripheral component (e.g., a cupholder) adjustable between first and second positions. In some embodiments of the example of the cupholder, the cupholder is configured to stay substantially level (e.g., and an object therein level, such as a beverage) regardless of the position of the adjustable gaming device (e.g., at the first position, the second position, and any positions therebetween). In other words, the cupholder may be able to adjust or reposition itself when the device is moved so that the cupholder and the drink held in the cupholder maintain their levelness.

Figure 6:
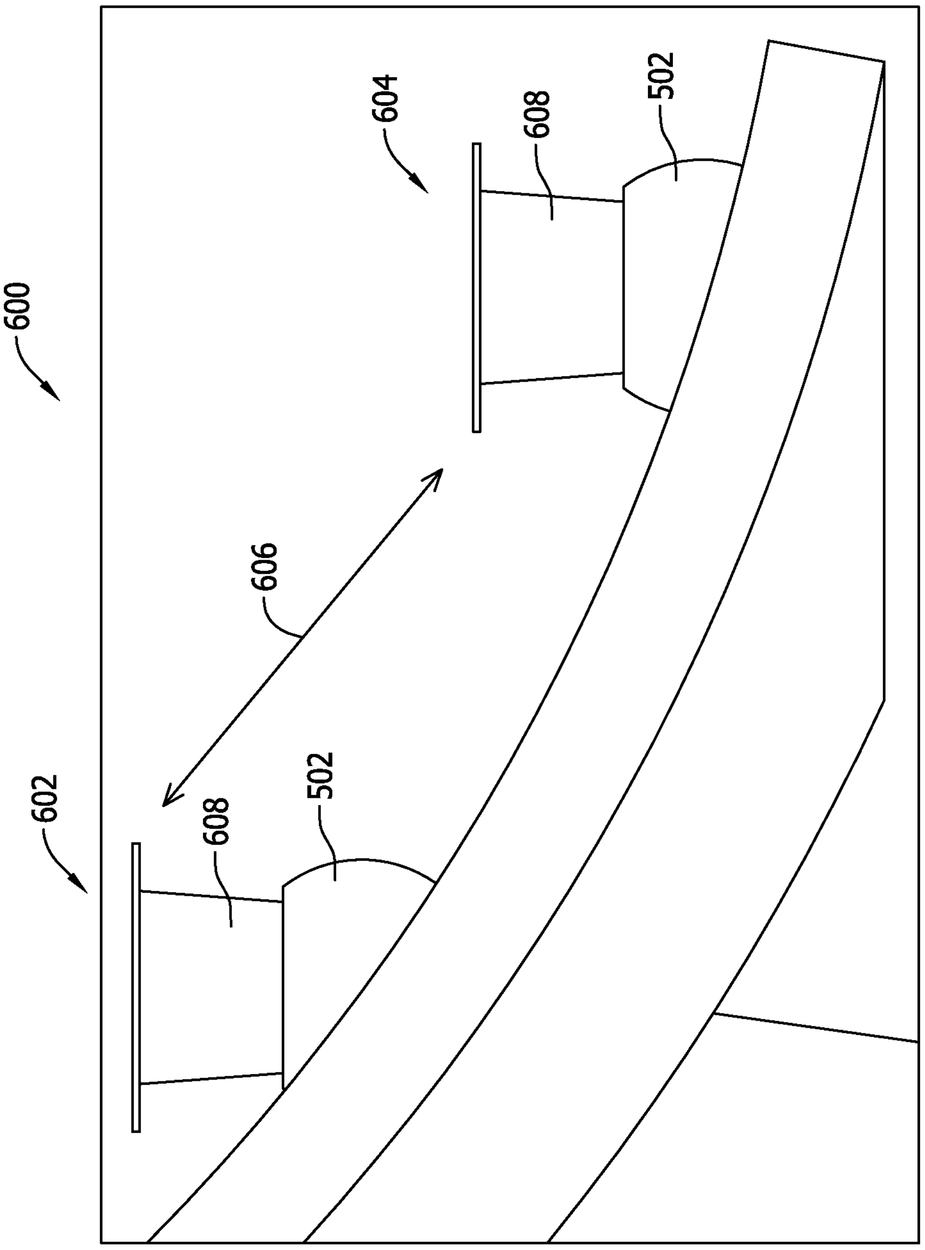
FIG. 6 illustrates a side view of a portion of the adjustable gaming device shown in FIG. 4.

For example, the cupholder may be rotatable such that the cupholder remains level based on a current position (e.g., angle) of the adjustable gaming device. In some embodiments, a screw may be positioned at the bottom of the cupholder and configured rotate the cupholder based on the current position of the adjustable gaming device. For instance, when the adjustable gaming device is in the first position, the screw may control the cupholder to be in a "lower" position while when the adjustable gaming device is in the second position the screw may control the cupholder to be in an "upper" position (e.g., see FIG. 6). In some embodiments, the cupholder may be configured to move up and down the adjustable gaming device (e.g., as shown in FIG. 6) while in some embodiments the cupholder may be configured to rotate in place in order to remain level.

One or more sensors may be utilized to determine a current position of the adjustable gaming device and a current position of the cupholder. For example, a current position of the adjustable gaming device may be identified and a desired position of the cupholder may be determined based on the current position of the adjustable gaming device (e.g., in real time). For example, a lookup table stored in memory may be utilized to determine a desired position of the cupholder based on a current position of the adjustable gaming device. The cupholder may then be controlled (e.g., by one or more processors) to move to the desired position. Notably, the timeliness with which the cupholder moves is important in order to, for example, keep a drink level as the adjustable gaming device moves.

In some embodiments, another means that is in addition to or alternative from a screw may be utilized to control a position of the cupholder. For example, in some embodiments the cupholder may rest on a spring-loaded ball and a user of the adjustable gaming device may be able to rotate/move the cupholder and/or "lock" the cupholder in place (e.g., by pressing a button) once the cupholder is in the desired position. In some embodiments, a gyroscope or similar device in communication with one or more processors may be utilized to identify a current position of the cupholder.

In some embodiments, the cupholder may also include a sensor (e.g., an optical sensor) utilized to identify when an object is positioned in the cupholder. For example, in some embodiments an identifier may be included on the adjustable gaming device (e.g., a designated light) to indicate whether an object is included in the cupholder or not. In some embodiments, whether or not an object is in the cupholder may be communicated to another device (e.g., a backend server). Thus, based on the identifier and/or communication to another device, casino floor staff, as an example, can easily identify when objects should be removed from the cupholder (e.g., no game is being played on the adjustable gaming device but an object remains in the cupholder).

The adjustable gaming device may also include a virtual button deck (e.g., including virtual and/or physical buttons). In some embodiments, the adjustable gaming device includes a disinfectant and/or ultraviolet (UV) light equipped cleaning apparatus configured to travel between first and second positions (e.g., across the virtual button deck and/or other components, such as a wireless device) for cleaning before and after player engagement. For example, the cleaning apparatus may automatically clean when the adjustable gaming device detects that a gaming session has ended or begun (e.g., based on a player card-in or card-out).

In some embodiments, the cleaning apparatus may be activated based on an input from a user of the adjustable gaming device (e.g., a player, a technician, etc.). For example, a button (e.g., virtual or physical) may be provided on the adjustable gaming device such that selection of the button causes the cleaning apparatus to activate and clean the button deck (e.g., or other aspect of the adjustable gaming device).

In some embodiments, activation may be controlled based on an input at a device in communication with the adjustable gaming device such as a backend server, another gaming device, or a mobile device. For instance, a backend server or other gaming device may control cleaning of one or more adjustable gaming devices (e.g., or other gaming devices) at predetermined times (e.g., based on a stored schedule) or at other stored or manually-selected times (e.g., before/after an event such as a tournament, at certain busy or slow times on a casino floor, etc.).

As noted above, in some embodiments the cleaning apparatus may be activated based on an input at a mobile device (e.g., in communication with the adjustable gaming device and associated with a player). For example, during play at the adjustable gaming device the player may select a button displayed at their mobile device (e.g., at a GUI caused to be displayed at the mobile device by the adjustable gaming device or backend server) that causes the adjustable gaming device to be activated (e.g., if the button deck appears dirty, in response to a spill, desired periodic cleaning, or any other reason). In some embodiments, a threshold amount of time may be required to pass (e.g., as tracked by the adjustable gaming device or a backend server) in between manual activations of the cleaning apparatus (e.g., to prevent repeated activation of the cleaning apparatus).

In some embodiments, a notification may be presented to a player at the adjustable gaming device when the cleaning apparatus is going to be activated. For example, a notification may appear on the adjustable gaming device or a mobile device of the player a predetermined amount of time before cleaning will occur (e.g., to give the player to, if desired, end the gaming session and begin play on another machine). In some embodiments, the player may be provided with an option to provide an input to bypass the cleaning (e.g., to prevent interruption of their gaming session). In some embodiments, only certain players are provided the option to bypass cleaning (e.g., players of a certain loyalty tier).

Other aspects of the adjustable gaming device, in addition to or alternatively from cleaning, may also be controlled by a device in communication with the adjustable gaming device (e.g., a backend server or other gaming device). For example, the adjustable gaming device may enter an attraction mode when no player is playing at the adjustable gaming device. Some embodiments of the attraction mode may include the adjustable gaming device moving between the first position and the second position and/or positions therebetween, as described herein (e.g., "bobbing" up and down to attract player attention). By the attract mode including movement of the adjustable gaming device between the first position and the second position, players are also made aware of the capability of the adjustable gaming device to move between the first position and the second position as desired by the player. Otherwise, for example, a player may consider playing or play at the adjustable gaming device without knowing about the option to adjust the adjustable gaming device between the first position and the second position (e.g., based on their preferences).

In some embodiments, the attract mode may also include display of certain messages and/or other displayed features (e.g., flashing lights) to attract player attention. In some embodiments, the attract mode may include display of a message regarding how recently the adjustable gaming device was cleaned (e.g., to notify potential players of the cleanliness of the adjustable gaming device and/or communicate the option for players to manually cause the cleaning apparatus to be activated). In some embodiments, the adjustable gaming device may vibrate when in the attract mode.

In some embodiments, a plurality of adjustable gaming devices may be controlled (e.g., by a device in communication with the adjustable gaming devices) to be in a synchronized attract mode. For example, a bank of adjustable gaming devices may move between the first and second positions such that the bank of adjustable gaming devices are at substantially the same position as they move between the first and second positions. In some embodiments, the adjustable gaming devices may move between the first and second positions in a staggered manner (e.g., to give an appearance of the adjustable gaming devices "doing the wave" similar to a crowd at an event).

Further, one or more adjustable gaming devices may be caused to be in a "celebration" mode. In some embodiments, the celebration mode is similar to the attract mode as described herein (e.g., movement of one or more adjustable gaming devices between first and second positions, flashing lights, certain messages being displayed, vibration of the one or more adjustable gaming devices etc.). For example, in response to a jackpot win or other big win on a casino floor at or near the one or more adjustable gaming devices, the one or more adjustable gaming devices may enter the celebration mode to communicate to other players on the casino floor of the win (e.g., or other trigger event) and attract attention.

FIG. 1 illustrates several different models of EGMs which may be networked to various gaming related servers. Shown is a system 100 in a gaming environment including one or more server computers 102 (e.g., slot servers of a casino) that are in communication, via a communications network, with one or more gaming devices 104A-104X (EGMs, slots, video poker, bingo machines, etc.) that can implement one or more aspects of the present disclosure. The gaming devices 104A-104X may alternatively be portable and/or remote gaming devices such as, but not limited to, a smart phone, a tablet, a laptop, or a game console. Gaming devices 104A-104X utilize specialized software and/or hardware to form non-generic, particular machines or apparatuses that comply with regulatory requirements regarding devices used for wagering or games of chance that provide monetary awards.

Communication between the gaming devices 104A-104X and the server computers 102, and among the gaming devices 104A-104X, may be direct or indirect using one or more communication protocols. As an example, gaming devices 104A-104X and the server computers 102 can communicate over one or more communication networks, such as over the Internet through a website maintained by a computer on a remote server or over an online data network including commercial online service providers, Internet service providers, private networks (e.g., local area networks and enterprise networks), and the like (e.g., wide area networks). The communication networks could allow gaming devices 104A-104X to communicate with one another and/or the server computers 102 using a variety of communication-based technologies, such as radio frequency (RF) (e.g., wireless fidelity (WiFi®) and Bluetooth®), cable TV, satellite links and the like.

In some implementation, server computers 102 may not be necessary and/or preferred. For example, in one or more implementations, a stand-alone gaming device such as gaming device 104A, gaming device 104B or any of the other gaming devices 104C-104X can implement one or more aspects of the present disclosure. However, it is typical to find multiple EGMs connected to networks implemented with one or more of the different server computers 102 described herein.

The server computers 102 may include a central determination gaming system server 106, a ticket-in-ticket-out (TITO) system server 108, a player tracking system server 110, a progressive system server 112, and/or a casino management system server 114. Gaming devices 104A-104X may include features to enable operation of any or all servers for use by the player and/or operator (e.g., the casino, resort, gaming establishment, tavern, pub, etc.). For example, game outcomes may be generated on a central determination gaming system server 106 and then transmitted over the network to any of a group of remote terminals or remote gaming devices 104A-104X that utilize the game outcomes and display the results to the players.

Gaming device 104A is often of a cabinet construction which may be aligned in rows or banks of similar devices for placement and operation on a casino floor. The gaming device 104A often includes a main door which provides access to the interior of the cabinet. Gaming device 104A typically includes a button area or button deck 120 accessible by a player that is configured with input switches or buttons 122, an access channel for a bill validator 124, and/or an access channel for a ticket-out printer 126.

In FIG. 1, gaming device 104A is shown as a Relm XL™ model gaming device manufactured by Aristocrat® Technologies, Inc. As shown, gaming device 104A is a reel machine having a gaming display area 118 comprising a number (typically 3 or 5) of mechanical reels 130 with various symbols displayed on them. The mechanical reels 130 are independently spun and stopped to show a set of symbols within the gaming display area 118 which may be used to determine an outcome to the game.

In many configurations, the gaming device 104A may have a main display 128 (e.g., video display monitor) mounted to, or above, the gaming display area 118. The main display 128 can be a high-resolution liquid crystal display (LCD), plasma, light emitting diode (LED), or organic light emitting diode (OLED) panel which may be flat or curved as shown, a cathode ray tube, or other conventional electronically controlled video monitor.

In some implementations, the bill validator 124 may also function as a "ticket-in" reader that allows the player to use a casino issued credit ticket to load credits onto the gaming device 104A (e.g., in a cashless ticket ("TITO") system). In such cashless implementations, the gaming device 104A may also include a "ticket-out" printer 126 for outputting a credit ticket when a "cash out" button is pressed. Cashless TITO systems are used to generate and track unique barcodes or other indicators printed on tickets to allow players to avoid the use of bills and coins by loading credits using a ticket reader and cashing out credits using a ticket-out printer 126 on the gaming device 104A. The gaming device 104A can have hardware meters for purposes including ensuring regulatory compliance and monitoring the player credit balance. In addition, there can be additional meters that record the total amount of money wagered on the gaming device, total amount of money deposited, total amount of money withdrawn, total amount of winnings on gaming device 104A.

In some implementations, a player tracking card reader 144, a transceiver for wireless communication with a mobile device (e.g., a player's smartphone), a keypad 146, and/or an illuminated display 148 for reading, receiving, entering, and/or displaying player tracking information is provided in gaming device 104A. In such implementations, a game controller within the gaming device 104A can communicate with the player tracking system server 110 to send and receive player tracking information.

Gaming device 104A may also include a bonus topper wheel 134. When bonus play is triggered (e.g., by a player achieving a particular outcome or set of outcomes in the primary game), bonus topper wheel 134 is operative to spin and stop with indicator arrow 136 indicating the outcome of the bonus game. Bonus topper wheel 134 is typically used to play a bonus game, but it could also be incorporated into play of the base or primary game.

A candle 138 may be mounted on the top of gaming device 104A and may be activated by a player (e.g., using a switch or one of buttons 122) to indicate to operations staff that gaming device 104A has experienced a malfunction or the player requires service. The candle 138 is also often used to indicate a jackpot has been won and to alert staff that a hand payout of an award may be needed.

There may also be one or more information panels 152 which may be a back-lit, silkscreened glass panel with lettering to indicate general game information including, for example, a game denomination (e.g., $0.25 or $1), pay lines, pay tables, and/or various game related graphics. In some implementations, the information panel(s) 152 may be implemented as an additional video display.

Gaming devices 104A have traditionally also included a handle 132 typically mounted to the side of main cabinet 116 which may be used to initiate game play.

Figure 2A:
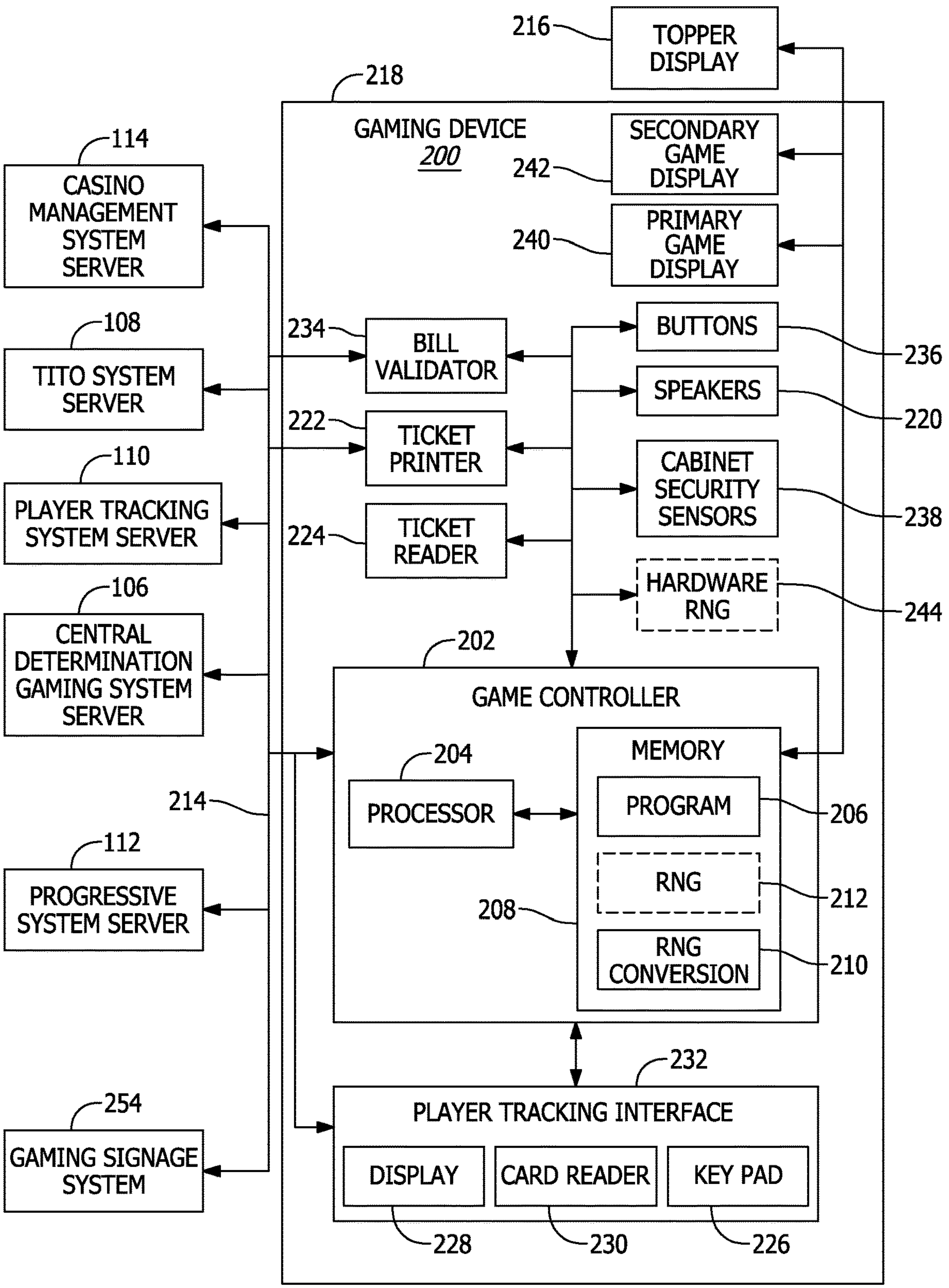
FIG. 2A is a block diagram showing various functional elements of an exemplary EGM.

Many or all the above described components can be controlled by circuitry (e.g., a game controller) housed inside the main cabinet 116 of the gaming device 104A, the details of which are shown in FIG. 2A.

An alternative example gaming device 104B illustrated in FIG. 1 is the Arc™ model gaming device manufactured by Aristocrat® Technologies, Inc. Note that where possible, reference numerals identifying similar features of the gaming device 104A implementation are also identified in the gaming device 104B implementation using the same reference numbers. Gaming device 104B does not include physical reels and instead shows game play functions on main display 128. An optional topper screen 140 may be used as a secondary game display for bonus play, to show game features or attraction activities while a game is not in play, or any other information or media desired by the game designer or operator. In some implementations, the optional topper screen 140 may also or alternatively be used to display progressive jackpot prizes available to a player during play of gaming device 104B.

Example gaming device 104B includes a main cabinet 116 including a main door which opens to provide access to the interior of the gaming device 104B. The main or service door is typically used by service personnel to refill the ticket-out printer 126 and collect bills and tickets inserted into the bill validator 124. The main or service door may also be accessed to reset the machine, verify and/or upgrade the software, and for general maintenance operations.

Another example gaming device 104C shown is the Helix™ model gaming device manufactured by Aristocrat® Technologies, Inc. Gaming device 104C includes a main display 128A that is in a landscape orientation. Although not illustrated by the front view provided, the main display 128A may have a curvature radius from top to bottom, or alternatively from side to side. In some implementations, main display 128A is a flat panel display. Main display 128A is typically used for primary game play while secondary display 128B is typically used for bonus game play, to show game features or attraction activities while the game is not in play or any other information or media desired by the game designer or operator. In some implementations, example gaming device 104C may also include speakers 142 to output various audio such as game sound, background music, etc.

Many different types of games, including mechanical slot games, video slot games, video poker, video black jack, video pachinko, keno, bingo, and lottery, may be provided with or implemented within the depicted gaming devices 104A-104C and other similar gaming devices. Each gaming device may also be operable to provide many different games. Games may be differentiated according to themes, sounds, graphics, type of game (e.g., slot game vs. card game vs. game with aspects of skill), denomination, number of paylines, maximum jackpot, progressive or non-progressive, bonus games, and may be deployed for operation in Class 2 or Class 3, etc.

FIG. 2A is a block diagram depicting exemplary internal electronic components of a gaming device 200 connected to various external systems. All or parts of the gaming device 200 shown could be used to implement any one of the example gaming devices 104A-X depicted in FIG. 1. As shown in FIG. 2A, gaming device 200 includes a topper display 216 or another form of a top box (e.g., a topper wheel, a topper screen, etc.) that sits above cabinet 218. Cabinet 218 or topper display 216 may also house a number of other components which may be used to add features to a game being played on gaming device 200, including speakers 220, a ticket printer 222 which prints bar-coded tickets or other media or mechanisms for storing or indicating a player's credit value, a ticket reader 224 which reads bar-coded tickets or other media or mechanisms for storing or indicating a player's credit value, and a player tracking interface 232. Player tracking interface 232 may include a keypad 226 for entering information, a player tracking display 228 for displaying information (e.g., an illuminated or video display), a card reader 230 for receiving data and/or communicating information to and from media or a device such as a smart phone enabling player tracking. FIG. 2 also depicts utilizing a ticket printer 222 to print tickets for a TITO system server 108. Gaming device 200 may further include a bill validator 234, player-input buttons 236 for player input, cabinet security sensors 238 to detect unauthorized opening of the cabinet 218, a primary game display 240, and a secondary game display 242, each coupled to and operable under the control of game controller 202.

The games available for play on the gaming device 200 are controlled by a game controller 202 that includes one or more processors 204. Processor 204 represents a general-purpose processor, a specialized processor intended to perform certain functional tasks, or a combination thereof. As an example, processor 204 can be a central processing unit (CPU) that has one or more multi-core processing units and memory mediums (e.g., cache memory) that function as buffers and/or temporary storage for data. Alternatively, processor 204 can be a specialized processor, such as an application specific integrated circuit (ASIC), graphics processing unit (GPU), field-programmable gate array (FPGA), digital signal processor (DSP), or another type of hardware accelerator. In another example, processor 204 is a system on chip (SoC) that combines and integrates one or more general-purpose processors and/or one or more specialized processors. Although FIG. 2A illustrates that game controller 202 includes a single processor 204, game controller 202 is not limited to this representation and instead can include multiple processors 204 (e.g., two or more processors).

FIG. 2A illustrates that processor 204 is operatively coupled to memory 208. Memory 208 is defined herein as including volatile and nonvolatile memory and other types of non-transitory data storage components. Volatile memory is memory that do not retain data values upon loss of power. Nonvolatile memory is memory that do retain data upon a loss of power. Examples of memory 208 include random access memory (RAM), read-only memory (ROM), hard disk drives, solid-state drives, universal serial bus (USB) flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, examples of RAM include static random access memory (SRAM), dynamic random access memory (DRAM), magnetic random access memory (MRAM), and other such devices. Examples of ROM include a programmable read-only memory (PROM), an erasable programmable read-only memory (EPROM), an electrically erasable programmable read-only memory (EEPROM), or other like memory device. Even though FIG. 2A illustrates that game controller 202 includes a single memory 208, game controller 202 could include multiple memories 208 for storing program instructions and/or data.

Memory 208 can store one or more game programs 206 that provide program instructions and/or data for carrying out various implementations (e.g., game mechanics) described herein. Stated another way, game program 206 represents an executable program stored in any portion or component of memory 208. In one or more implementations, game program 206 is embodied in the form of source code that includes human-readable statements written in a programming language or machine code that contains numerical instructions recognizable by a suitable execution system, such as a processor 204 in a game controller or other system. Examples of executable programs include: (1) a compiled program that can be translated into machine code in a format that can be loaded into a random access portion of memory 208 and run by processor 204; (2) source code that may be expressed in proper format such as object code that is capable of being loaded into a random access portion of memory 208 and executed by processor 204; and (3) source code that may be interpreted by another executable program to generate instructions in a random access portion of memory 208 to be executed by processor 204.

Alternatively, game programs 206 can be set up to generate one or more game instances based on instructions and/or data that gaming device 200 exchanges with one or more remote gaming devices, such as a central determination gaming system server 106 (not shown in FIG. 2A but shown in FIG. 1). For purpose of this disclosure, the term "game instance" refers to a play or a round of a game that gaming device 200 presents (e.g., via a user interface (UI)) to a player. The game instance is communicated to gaming device 200 via the network 214 and then displayed on gaming device 200. For example, gaming device 200 may execute game program 206 as video streaming software that allows the game to be displayed on gaming device 200. When a game is stored on gaming device 200, it may be loaded from memory 208 (e.g., from a read only memory (ROM)) or from the central determination gaming system server 106 to memory 208.

Gaming devices, such as gaming device 200, are highly regulated to ensure fairness and, in many cases, gaming device 200 is operable to award monetary awards (e.g., typically dispensed in the form of a redeemable voucher). Therefore, to satisfy security and regulatory requirements in a gaming environment, hardware and software architectures are implemented in gaming devices 200 that differ significantly from those of general-purpose computers. Adapting general purpose computers to function as gaming devices 200 is not simple or straightforward because of: (1) the regulatory requirements for gaming devices 200, (2) the harsh environment in which gaming devices 200 operate, (3) security requirements, (4) fault tolerance requirements, and (5) the requirement for additional special purpose componentry enabling functionality of an EGM. These differences require substantial engineering effort with respect to game design implementation, game mechanics, hardware components, and software.

One regulatory requirement for games running on gaming device 200 generally involves complying with a certain level of randomness. Typically, gaming jurisdictions mandate that gaming devices 200 satisfy a minimum level of randomness without specifying how a gaming device 200 should achieve this level of randomness. To comply, FIG. 2A illustrates that gaming device 200 could include an RNG 212 that utilizes hardware and/or software to generate RNG outcomes that lack any pattern. The RNG operations are often specialized and non-generic in order to comply with regulatory and gaming requirements. For example, in a slot game, game program 206 can initiate multiple RNG calls to RNG 212 to generate RNG outcomes, where each RNG call and RNG outcome corresponds to an outcome for a reel. In another example, gaming device 200 can be a Class II gaming device where RNG 212 generates RNG outcomes for creating Bingo cards. In one or more implementations, RNG 212 could be one of a set of RNGs operating on gaming device 200. More generally, an output of the RNG 212 can be the basis on which game outcomes are determined by the game controller 202. Game developers could vary the degree of true randomness for each RNG (e.g., pseudorandom) and utilize specific RNGs depending on game requirements. The output of the RNG 212 can include a random number or pseudorandom number (either is generally referred to as a "random number").

In FIG. 2A, RNG 212 and hardware RNG 244 are shown in dashed lines to illustrate that RNG 212, hardware RNG 244, or both can be included in gaming device 200. In one implementation, instead of including RNG 212, gaming device 200 could include a hardware RNG 244 that generates RNG outcomes. Analogous to RNG 212, hardware RNG 244 performs specialized and non-generic operations in order to comply with regulatory and gaming requirements. For example, because of regulation requirements, hardware RNG 244 could be a random number generator that securely produces random numbers for cryptography use. The gaming device 200 then uses the secure random numbers to generate game outcomes for one or more game features. In another implementation, the gaming device 200 could include both hardware RNG 244 and RNG 212. RNG 212 may utilize the RNG outcomes from hardware RNG 244 as one of many sources of entropy for generating secure random numbers for the game features.

Another regulatory requirement for running games on gaming device 200 includes ensuring a certain level of RTP. Similar to the randomness requirement discussed above, numerous gaming jurisdictions also mandate that gaming device 200 provides a minimum level of RTP (e.g., RTP of at least 75%). A game can use one or more lookup tables (also called weighted tables) as part of a technical solution that satisfies regulatory requirements for randomness and RTP. In particular, a lookup table can integrate game features (e.g., trigger events for special modes or bonus games; newly introduced game elements such as extra reels, new symbols, or new cards; stop positions for dynamic game elements such as spinning reels, spinning wheels, or shifting reels; or card selections from a deck) with random numbers generated by one or more RNGs, so as to achieve a given level of volatility for a target level of RTP. (In general, volatility refers to the frequency or probability of an event such as a special mode, payout, etc. For example, for a target level of RTP, a higher-volatility game may have a lower payout most of the time with an occasional bonus having a very high payout, while a lower-volatility game has a steadier payout with more frequent bonuses of smaller amounts.) Configuring a lookup table can involve engineering decisions with respect to how RNG outcomes are mapped to game outcomes for a given game feature, while still satisfying regulatory requirements for RTP. Configuring a lookup table can also involve engineering decisions about whether different game features are combined in a given entry of the lookup table or split between different entries (for the respective game features), while still satisfying regulatory requirements for RTP and allowing for varying levels of game volatility.

FIG. 2A illustrates that gaming device 200 includes an RNG conversion engine 210 that translates the RNG outcome from RNG 212 to a game outcome presented to a player. To meet a designated RTP, a game developer can set up the RNG conversion engine 210 to utilize one or more lookup tables to translate the RNG outcome to a symbol element, stop position on a reel strip layout, and/or randomly chosen aspect of a game feature. As an example, the lookup tables can regulate a prize payout amount for each RNG outcome and how often the gaming device 200 pays out the prize payout amounts. The RNG conversion engine 210 could utilize one lookup table to map the RNG outcome to a game outcome displayed to a player and a second lookup table as a pay table for determining the prize payout amount for each game outcome. The mapping between the RNG outcome to the game outcome controls the frequency in hitting certain prize payout amounts.

FIG. 2A also depicts that gaming device 200 is connected over network 214 to player tracking system server 110. Player tracking system server 110 may be, for example, an OASIS® system manufactured by Aristocrat® Technologies, Inc. Player tracking system server 110 is used to track play (e.g. amount wagered, games played, time of play and/or other quantitative or qualitative measures) for individual players so that an operator may reward players in a loyalty program. The player may use the player tracking interface 232 to access his/her account information, activate free play, and/or request various information. Player tracking or loyalty programs seek to reward players for their play and help build brand loyalty to the gaming establishment. The rewards typically correspond to the player's level of patronage (e.g., to the player's playing frequency and/or total amount of game plays at a given casino). Player tracking rewards may be complimentary and/or discounted meals, lodging, entertainment and/or additional play. Player tracking information may be combined with other information that is now readily obtainable by a casino management system.

When a player wishes to play the gaming device 200, he/she can insert cash or a ticket voucher through a coin acceptor (not shown) or bill validator 234 to establish a credit balance on the gaming device. The credit balance is used by the player to place wagers on instances of the game and to receive credit awards based on the outcome of winning instances. The credit balance is decreased by the amount of each wager and increased upon a win. The player can add additional credits to the balance at any time. The player may also optionally insert a loyalty club card into the card reader 230. During the game, the player views with one or more UIs, the game outcome on one or more of the primary game display 240 and secondary game display 242. Other game and prize information may also be displayed.

For each game instance, a player may make selections, which may affect play of the game. For example, the player may vary the total amount wagered by selecting the amount bet per line and the number of lines played. In many games, the player is asked to initiate or select options during course of game play (such as spinning a wheel to begin a bonus round or select various items during a feature game). The player may make these selections using the player-input buttons 236, the primary game display 240 which may be a touch screen, or using some other device which enables a player to input information into the gaming device 200.

During certain game events, the gaming device 200 may display visual and auditory effects that can be perceived by the player. These effects add to the excitement of a game, which makes a player more likely to enjoy the playing experience. Auditory effects include various sounds that are projected by the speakers 220. Visual effects include flashing lights, strobing lights or other patterns displayed from lights on the gaming device 200 or from lights behind the information panel 152 (FIG. 1).

When the player is done, he/she cashes out the credit balance (typically by pressing a cash out button to receive a ticket from the ticket printer 222). The ticket may be "cashed-in" for money or inserted into another machine to establish a credit balance for play.

Additionally, or alternatively, gaming devices 104A-104X and 200 can include or be coupled to one or more wireless transmitters, receivers, and/or transceivers (not shown in FIGS. 1 and 2A) that communicate (e.g., Bluetooth® or other near-field communication technology) with one or more mobile devices to perform a variety of wireless operations in a casino environment. Examples of wireless operations in a casino environment include detecting the presence of mobile devices, performing credit, points, comps, or other marketing or hard currency transfers, establishing wagering sessions, and/or providing a personalized casino-based experience using a mobile application. In one implementation, to perform these wireless operations, a wireless transmitter or transceiver initiates a secure wireless connection between a gaming device 104A-104X and 200 and a mobile device. After establishing a secure wireless connection between the gaming device 104A-104X and 200 and the mobile device, the wireless transmitter or transceiver does not send and/or receive application data to and/or from the mobile device. Rather, the mobile device communicates with gaming devices 104A-104X and 200 using another wireless connection (e.g., WiFi® or cellular network). In another implementation, a wireless transceiver establishes a secure connection to directly communicate with the mobile device. The mobile device and gaming device 104A-104X and 200 sends and receives data utilizing the wireless transceiver instead of utilizing an external network. For example, the mobile device would perform digital wallet transactions by directly communicating with the wireless transceiver. In one or more implementations, a wireless transmitter could broadcast data received by one or more mobile devices without establishing a pairing connection with the mobile devices.

Although FIGS. 1 and 2A illustrate specific implementations of a gaming device (e.g., gaming devices 104A-104X and 200), the disclosure is not limited to those implementations shown in FIGS. 1 and 2. For example, not all gaming devices suitable for implementing implementations of the present disclosure necessarily include top wheels, top boxes, information panels, cashless ticket systems, and/or player tracking systems. Further, some suitable gaming devices have only a single game display that includes only a mechanical set of reels and/or a video display, while others are designed for bar counters or tabletops and have displays that face upwards. Gaming devices 104A-104X and 200 may also include other processors that are not separately shown. Using FIG. 2A as an example, gaming device 200 could include display controllers (not shown in FIG. 2A) configured to receive video input signals or instructions to display images on game displays 240 and 242. Alternatively, such display controllers may be integrated into the game controller 202. The use and discussion of FIGS. 1 and 2 are examples to facilitate ease of description and explanation.

Figure 2B:
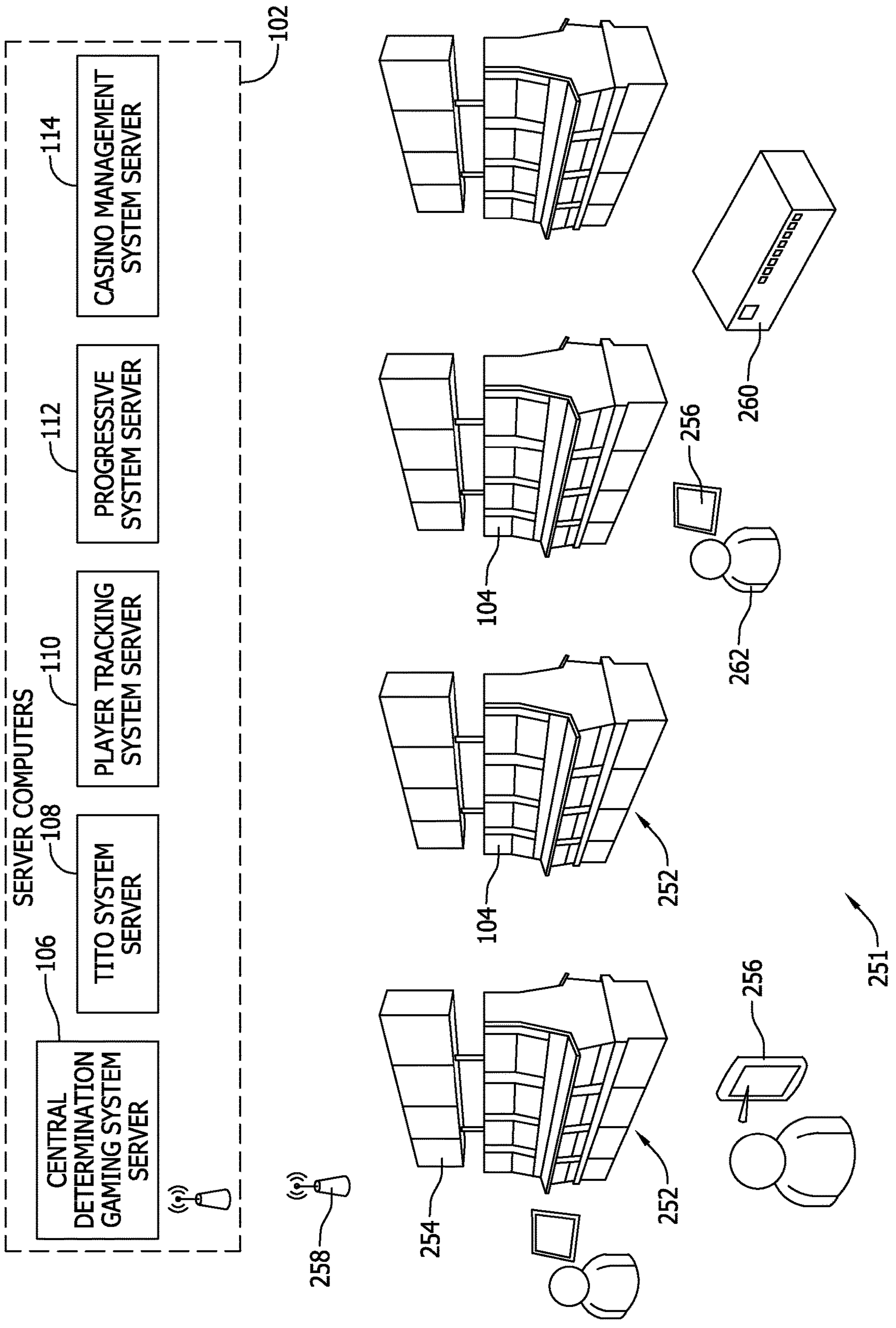
FIG. 2B depicts a casino gaming environment according to one example.

FIG. 2B depicts a casino gaming environment according to one example. In this example, the casino 251 includes banks 252 of EGMs 104. In this example, each bank 252 of EGMs 104 includes a corresponding gaming signage system 254 (also shown in FIG. 2A). According to this implementation, the casino 251 also includes mobile gaming devices 256, which are also configured to present wagering games in this example. The mobile gaming devices 256 may, for example, include tablet devices, cellular phones, smart phones and/or other handheld devices. In this example, the mobile gaming devices 256 are configured for communication with one or more other devices in the casino 251, including but not limited to one or more of the server computers 102, via wireless access points 258.

According to some examples, the mobile gaming devices 256 may be configured for stand-alone determination of game outcomes. However, in some alternative implementations the mobile gaming devices 256 may be configured to receive game outcomes from another device, such as the central determination gaming system server 106, one of the EGMs 104, etc.

Some mobile gaming devices 256 may be configured to accept monetary credits from a credit or debit card, via a wireless interface (e.g., via a wireless payment app), via tickets, via a patron casino account, etc. However, some mobile gaming devices 256 may not be configured to accept monetary credits via a credit or debit card. Some mobile gaming devices 256 may include a ticket reader and/or a ticket printer whereas some mobile gaming devices 256 may not, depending on the particular implementation.

In some implementations, the casino 251 may include one or more kiosks 260 that are configured to facilitate monetary transactions involving the mobile gaming devices 256, which may include cash out and/or cash in transactions. The kiosks 260 may be configured for wired and/or wireless communication with the mobile gaming devices 256. The kiosks 260 may be configured to accept monetary credits from casino patrons 262 and/or to dispense monetary credits to casino patrons 262 via cash, a credit or debit card, via a wireless interface (e.g., via a wireless payment app), via tickets, etc. According to some examples, the kiosks 260 may be configured to accept monetary credits from a casino patron and to provide a corresponding amount of monetary credits to a mobile gaming device 256 for wagering purposes, e.g., via a wireless link such as a near-field communications link. In some such examples, when a casino patron 262 is ready to cash out, the casino patron 262 may select a cash out option provided by a mobile gaming device 256, which may include a real button or a virtual button (e.g., a button provided via a graphical user interface) in some instances. In some such examples, the mobile gaming device 256 may send a "cash out" signal to a kiosk 260 via a wireless link in response to receiving a "cash out" indication from a casino patron. The kiosk 260 may provide monetary credits to the casino patron 262 corresponding to the "cash out" signal, which may be in the form of cash, a credit ticket, a credit transmitted to a financial account corresponding to the casino patron, etc.

In some implementations, a cash-in process and/or a cash-out process may be facilitated by the TITO system server 108. For example, the TITO system server 108 may control, or at least authorize, ticket-in and ticket-out transactions that involve a mobile gaming device 256 and/or a kiosk 260.

Some mobile gaming devices 256 may be configured for receiving and/or transmitting player loyalty information. For example, some mobile gaming devices 256 may be configured for wireless communication with the player tracking system server 110. Some mobile gaming devices 256 may be configured for receiving and/or transmitting player loyalty information via wireless communication with a patron's player loyalty card, a patron's smartphone, etc.

According to some implementations, a mobile gaming device 256 may be configured to provide safeguards that prevent the mobile gaming device 256 from being used by an unauthorized person. For example, some mobile gaming devices 256 may include one or more biometric sensors and may be configured to receive input via the biometric sensor (s) to verify the identity of an authorized patron. Some mobile gaming devices 256 may be configured to function only within a predetermined or configurable area, such as a casino gaming area.

Figure 2C:
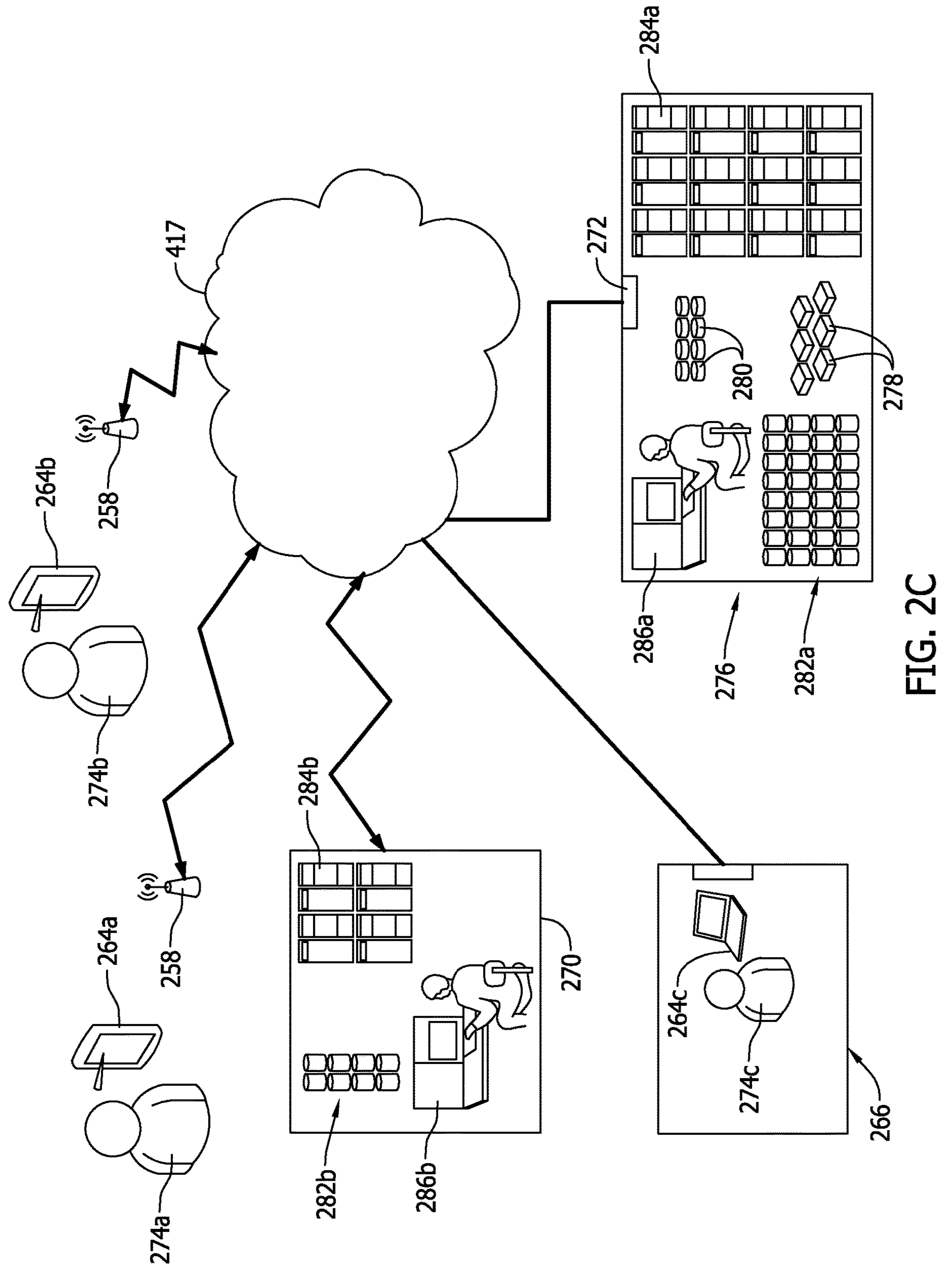
FIG. 2C is a diagram that shows examples of components of a system for providing online gaming according to some aspects of the present disclosure.

FIG. 2C is a diagram that shows examples of components of a system for providing online gaming according to some aspects of the present disclosure. As with other figures presented in this disclosure, the numbers, types and arrangements of gaming devices shown in FIG. 2C are merely shown by way of example. In this example, various gaming devices, including but not limited to end user devices (EUDs) 264*a*, 264*b* and 264*c* are capable of communication via one or more networks 417. The networks 417 may, for example, include one or more cellular telephone networks, the Internet, etc. In this example, the EUDs 264*a* and 264*b* are mobile devices: according to this example the EUD 264*a* is a tablet device and the EUD 264*b* is a smart phone. In this implementation, the EUD 264*c* is a laptop computer that is located within a residence 266 at the time depicted in FIG. 2C. Accordingly, in this example the hardware of EUDs is not specifically configured for online gaming, although each EUD is configured with software for online gaming. For example, each EUD may be configured with a web browser. Other implementations may include other types of EUD, some of which may be specifically configured for online gaming.

In this example, a gaming data center 276 includes various devices that are configured to provide online wagering games via the networks 417. The gaming data center 276 is capable of communication with the networks 417 via the gateway 272. In this example, switches 278 and routers 280 are configured to provide network connectivity for devices of the gaming data center 276, including storage devices 282*a*, servers 284*a* and one or more workstations 570*a*. The servers 284*a* may, for example, be configured to provide access to a library of games for online game play. In some examples, code for executing at least some of the games may initially be stored on one or more of the storage devices 282*a*. The code may be subsequently loaded onto a server 284*a* after selection by a player via an EUD and communication of that selection from the EUD via the networks 417. The server 284*a* onto which code for the selected game has been loaded may provide the game according to selections made by a player and indicated via the player's EUD. In other examples, code for executing at least some of the games may initially be stored on one or more of the servers 284*a*. Although only one gaming data center 276 is shown in FIG. 2C, some implementations may include multiple gaming data centers 276.

In this example, a financial institution data center 270 is also configured for communication via the networks 417. Here, the financial institution data center 270 includes servers 284*b*, storage devices 282*b*, and one or more workstations 286*b*. According to this example, the financial institution data center 270 is configured to maintain financial accounts, such as checking accounts, savings accounts, loan accounts, etc. In some implementations one or more of the authorized users 274*a*-274*c* may maintain at least one financial account with the financial institution that is serviced via the financial institution data center 270.

According to some implementations, the gaming data center 276 may be configured to provide online wagering games in which money may be won or lost. According to some such implementations, one or more of the servers 284*a* may be configured to monitor player credit balances, which may be expressed in game credits, in currency units, or in any other appropriate manner. In some implementations, the server(s) 284*a* may be configured to obtain financial credits from and/or provide financial credits to one or more financial institutions, according to a player's "cash in" selections, wagering game results and a player's "cash out" instructions. According to some such implementations, the server (s) 284*a* may be configured to electronically credit or debit the account of a player that is maintained by a financial institution, e.g., an account that is maintained via the financial institution data center 270. The server(s) 284*a* may, in some examples, be configured to maintain an audit record of such transactions.

In some alternative implementations, the gaming data center 276 may be configured to provide online wagering games for which credits may not be exchanged for cash or the equivalent. In some such examples, players may purchase game credits for online game play, but may not "cash out" for monetary credit after a gaming session. Moreover, although the financial institution data center 270 and the gaming data center 276 include their own servers and storage devices in this example, in some examples the financial institution data center 270 and/or the gaming data center 276 may use offsite "cloud-based" servers and/or storage devices. In some alternative examples, the financial institution data center 270 and/or the gaming data center 276 may rely entirely on cloud-based servers.

One or more types of devices in the gaming data center 276 (or elsewhere) may be capable of executing middleware, e.g., for data management and/or device communication. Authentication information, player tracking information, etc., including but not limited to information obtained by EUDs 264 and/or other information regarding authorized users of EUDs 264 (including but not limited to the authorized users 274*a*-274*c*), may be stored on storage devices 282 and/or servers 284. Other game-related information and/or software, such as information and/or software relating to leaderboards, players currently playing a game, game themes, game-related promotions, game competitions, etc., also may be stored on storage devices 282 and/or servers 284. In some implementations, some such game-related software may be available as "apps" and may be downloadable (e.g., from the gaming data center 276) by authorized users.

In some examples, authorized users and/or entities (such as representatives of gaming regulatory authorities) may obtain gaming-related information via the gaming data center 276. One or more other devices (such EUDs 264 or devices of the gaming data center 276) may act as intermediaries for such data feeds. Such devices may, for example, be capable of applying data filtering algorithms, executing data summary and/or analysis software, etc. In some implementations, data filtering, summary and/or analysis software may be available as "apps" and downloadable by authorized users.

Figure 3:
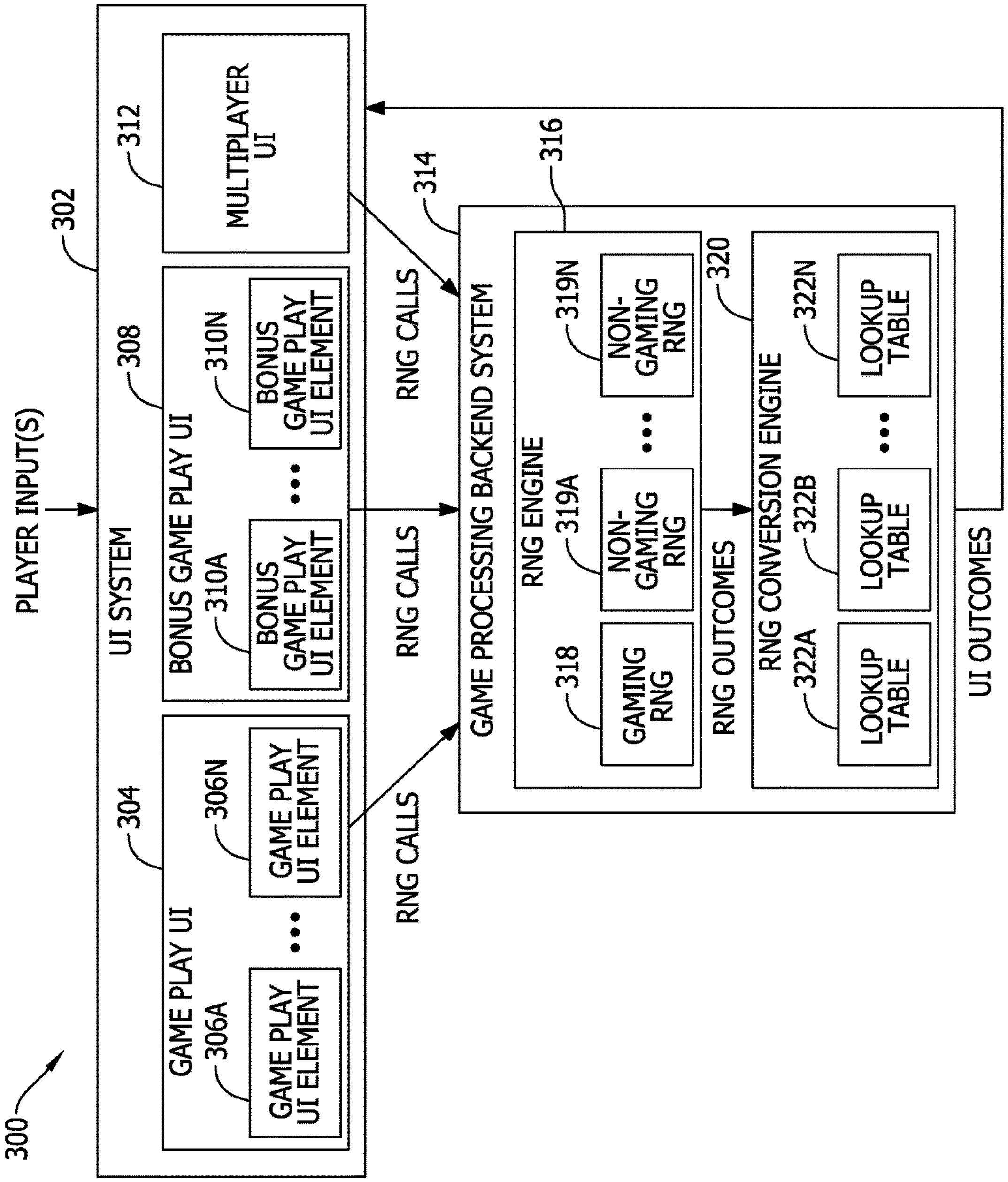
FIG. 3 illustrates, in block diagram form, an implementation of a game processing architecture algorithm that implements a game processing pipeline for the play of a game in accordance with various implementations described herein.

FIG. 3 illustrates, in block diagram form, an implementation of a game processing architecture 300 that implements a game processing pipeline for the play of a game in accordance with various implementations described herein. As shown in FIG. 3, the gaming processing pipeline starts with having a UI system 302 receive one or more player inputs for the game instance. Based on the player input(s), the UI system 302 generates and sends one or more RNG calls to a game processing backend system 314. Game processing backend system 314 then processes the RNG calls with RNG engine 316 to generate one or more RNG outcomes. The RNG outcomes are then sent to the RNG conversion engine 320 to generate one or more game outcomes for the UI system 302 to display to a player. The game processing architecture 300 can implement the game processing pipeline using a gaming device, such as gaming devices 104A-104X and 200 shown in FIGS. 1 and 2, respectively. Alternatively, portions of the gaming processing architecture 300 can implement the game processing pipeline using a gaming device and one or more remote gaming devices, such as central determination gaming system server 106 shown in FIG. 1.

The UI system 302 includes one or more UIs that a player can interact with. The UI system 302 could include one or more game play UIs 304, one or more bonus game play UIs 308, and one or more multiplayer UIs 312, where each UI type includes one or more mechanical UIs and/or graphical UIs (GUIs). In other words, game play UI 304, bonus game play UI 308, and the multiplayer UI 312 may utilize a variety of UI elements, such as mechanical UI elements (e.g., physical "spin" button or mechanical reels) and/or GUI elements (e.g., virtual reels shown on a video display or a virtual button deck) to receive player inputs and/or present game play to a player. Using FIG. 3 as an example, the different UI elements are shown as game play UI elements 306A-306N and bonus game play UI elements 310A-310N.

The game play UI 304 represents a UI that a player typically interfaces with for a base game. During a game instance of a base game, the game play UI elements 306A-306N (e.g., GUI elements depicting one or more virtual reels) are shown and/or made available to a user. In a subsequent game instance, the UI system 302 could transition out of the base game to one or more bonus games. The bonus game play UI 308 represents a UI that utilizes bonus game play UI elements 310A-310N for a player to interact with and/or view during a bonus game. In one or more implementations, at least some of the game play UI element 306A-306N are similar to the bonus game play UI elements 310A-310N. In other implementations, the game play UI element 306A-306N can differ from the bonus game play UI elements 310A-310N.

FIG. 3 also illustrates that UI system 302 could include a multiplayer UI 312 purposed for game play that differs or is separate from the typical base game. For example, multiplayer UI 312 could be set up to receive player inputs and/or presents game play information relating to a tournament mode. When a gaming device transitions from a primary game mode that presents the base game to a tournament mode, a single gaming device is linked and synchronized to other gaming devices to generate a tournament outcome. For example, multiple RNG engines 316 corresponding to each gaming device could be collectively linked to determine a tournament outcome. To enhance a player's gaming experience, tournament mode can modify and synchronize sound, music, reel spin speed, and/or other operations of the gaming devices according to the tournament game play. After tournament game play ends, operators can switch back the gaming device from tournament mode to a primary game mode to present the base game. Although FIG. 3 does not explicitly depict that multiplayer UI 312 includes UI elements, multiplayer UI 312 could also include one or more multiplayer UI elements.

Based on the player inputs, the UI system 302 could generate RNG calls to a game processing backend system 314. As an example, the UI system 302 could use one or more application programming interfaces (APIs) to generate the RNG calls. To process the RNG calls, the RNG engine 316 could utilize gaming RNG 318 and/or non-gaming RNGs 319A-319N. Gaming RNG 318 could corresponds to RNG 212 or hardware RNG 244 shown in FIG. 2A. As previously discussed with reference to FIG. 2A, gaming RNG 318 often performs specialized and non-generic operations that comply with regulatory and/or game requirements. For example, because of regulation requirements, gaming RNG 318 could correspond to RNG 212 by being a cryptographic RNG or pseudorandom number generator (PRNG) (e.g., Fortuna PRNG) that securely produces random numbers for one or more game features. To securely generate random numbers, gaming RNG 318 could collect random data from various sources of entropy, such as from an operating system (OS) and/or a hardware RNG (e.g., hardware RNG 244 shown in FIG. 2A). Alternatively, non-gaming RNGs 319A-319N may not be cryptographically secure and/or be computationally less expensive. Non-gaming RNGs 319A-319N can, thus, be used to generate outcomes for non-gaming purposes. As an example, non-gaming RNGs 319A-319N can generate random numbers for generating random messages that appear on the gaming device.

The RNG conversion engine 320 processes each RNG outcome from RNG engine 316 and converts the RNG outcome to a UI outcome that is feedback to the UI system 302. With reference to FIG. 2A, RNG conversion engine 320 corresponds to RNG conversion engine 210 used for game play. As previously described, RNG conversion engine 320 translates the RNG outcome from the RNG 212 to a game outcome presented to a player. RNG conversion engine 320 utilizes one or more lookup tables 322A-322N to regulate a prize payout amount for each RNG outcome and how often the gaming device pays out the derived prize payout amounts. In one example, the RNG conversion engine 320 could utilize one lookup table to map the RNG outcome to a game outcome displayed to a player and a second lookup table as a pay table for determining the prize payout amount for each game outcome. In this example, the mapping between the RNG outcome and the game outcome controls the frequency in hitting certain prize payout amounts. Different lookup tables could be utilized depending on the different game modes, for example, a base game versus a bonus game.

After generating the UI outcome, the game processing backend system 314 sends the UI outcome to the UI system 302. Examples of UI outcomes are symbols to display on a video reel or reel stops for a mechanical reel. In one example, if the UI outcome is for a base game, the UI system 302 updates one or more game play UI elements 306A-306N, such as symbols, for the game play UI 304. In another example, if the UI outcome is for a bonus game, the UI system could update one or more bonus game play UI elements 310A-310N (e.g., symbols) for the bonus game play UI 308. In response to updating the appropriate UI, the player may subsequently provide additional player inputs to initiate a subsequent game instance that progresses through the game processing pipeline.

Figure 4:
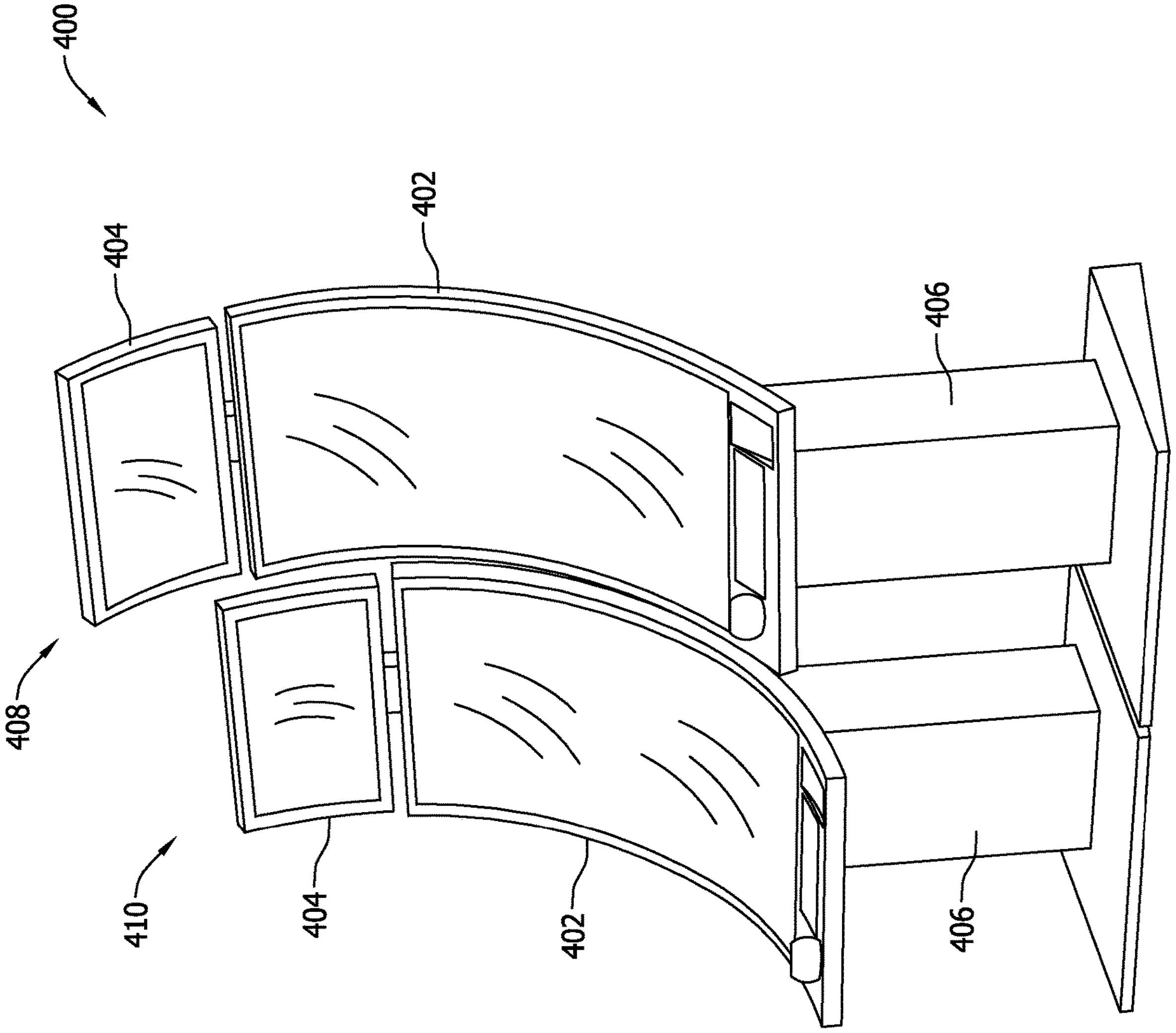
FIG. 4 illustrates an example adjustable gaming device in accordance with the present disclosure.

FIG. 4 illustrates an example adjustable gaming device 400 in accordance with the present disclosure. Adjustable gaming device 400 may be similar to gaming devices 104A-104X and include components/features of gaming devices 104A-104X as described herein. As shown in FIG. 4, adjustable gaming device 400 includes a main display device 402 (e.g., display 128), a secondary display device 404 (e.g., topper screen 140), and a base 406. Notably, adjustable gaming device 400 is shown in a first position 408 and a second position 410.

In the example embodiment, adjustable gaming device 400 or portion thereof (e.g., display devices 402, 404) is adjustable between first position 408 and second position 410. In the example shown in FIG. 4, first position 408 is a substantially upright/vertical position (e.g., wherein a bottom edge of display device 402 is proximate base 406) while second position 410 is a substantially slanted position (e.g., wherein the bottom edge of display device 402 is positioned away from base 406). For example, first position 408 (e.g., substantially upright/vertical wherein a top edge of display device 402 is higher than the top edge in second position 410) may be desirable for some players playing while standing at adjustable gaming device 400, while second position 410 (e.g., substantially slanted position) may be desirable for players playing while hunched over or seated at adjustable gaming device 400.

Display device 402 of adjustable gaming device 400 may be coupled to base 406 of adjustable gaming device 400 by an adjustable/moveable coupling mechanism (not shown) configured to facilitate movement of display device 402 between first position 408 and second position 410. As an example, the adjustable coupling mechanism may include a gearing system including a pinion/barrel that rolls along an arcuate track (e.g., teeth, rails, etc.) to control movement of display device 402. In some embodiments, the adjustable coupling mechanism includes rods that follow a sleeve along an arcuate path. In some embodiments, the gearing system includes a motor that controls movement of the pinion (e.g., in response to an input, for example at a button of adjustable gaming device 400). In some embodiments, the gearing system includes no motor (e.g., movement of display device 402 may be controlled manually by a user applying force to display device 402 (or housing thereof) or the gearing system). In some embodiments, a cable system, a hydraulic system, a pneumatic system, and/or any other system may be utilized to move display device 402 between first position 408 and second position 410.

In some embodiments, the gearing system includes a release mechanism configured to lock and/or unlock the gearing system. For example, when the release is locked, the gearing system does not allow movement of display device 402. When the release is unlocked, the gearing system allows movement of display device 402 (e.g., similar to the lever of an office chair that locks/unlocks to control chair height). In the example shown in FIG. 4, display device 404 is coupled to display device 402 and thus moves with display device 402 between first position 408 and second position 410. In some embodiments, other lifting/sliding mechanisms that are envisioned.

In some embodiments, adjustable gaming device 400 is configured to automatically move between first position 408, second position 410, or any position therebetween. For example, a player may input a player tracking card (or any identifying input, such as connecting a mobile device) to adjustable gaming device 400. A lookup may then be performed (e.g., by adjustable gaming device 400 or a backend server in communication with adjustable gaming device 400) to identify a player account associated with the player and preferences included in the player account, such as a desired position of display device 402. Display device 402 may then automatically be caused to move to the desired position (e.g., a favorite position stored in the player account).

In some embodiments, the player preferences, such as a preferred position of display device 402, may be received from a mobile device of a player. In some embodiments, a control panel (e.g., including virtual buttons) may be displayed on the mobile device of the player (e.g., when the mobile device is connected to adjustable gaming device 400). Inputs at the control panel may then cause display device 402 to move between first position 408 and second position 410 (e.g., selection of a "+" button may cause display device 402 to move toward first position 408 while selection of a "–" button may cause display device 402 to move toward second position 410). In some embodiments, the control panel may be provided on display device 402 or any other device in communication with adjustable gaming device 400.

In some embodiments, buttons associated with other features of adjustable gaming device 400 may also be provided on the control panel (e.g., at a mobile device of a player or any device in communication with adjustable gaming device 400 such as display device 402). For example, selection of a cleaning button may cause a button deck of adjustable gaming device 400 to automatically be cleaned (e.g., cleaning of button deck 504, as described below).

In some embodiments, the position of adjustable gaming device 400 may be controlled by a device in communication with adjustable gaming device 400 and/or based on a status of adjustable gaming device. For example, adjustable gaming device 400 may be configured to automatically move to a predefined position when a gaming session ends at adjustable gaming device 400 (e.g., and no game is being played at adjustable gaming device 400). In some embodiments, adjustable gaming device 400 may automatically move to a predefined positions when service is required at adjustable gaming device 400 (e.g., so that adjustable gaming device 400 can easily be identified as requiring servicing). In some embodiments, adjustable gaming device 400 may be controlled to move for any reason (e.g., the preference of a casino floor manager at a backend server in communication with adjustable gaming device 400).

Other aspects of adjustable gaming device 400, in addition to or alternatively from cleaning, may also be controlled by a device in communication with adjustable gaming device 400 (e.g., a backend server or other gaming device). For example, adjustable gaming device 400 may enter an attraction mode when no player is playing at adjustable gaming device 400. Some embodiments of the attraction mode may include adjustable gaming device 400 moving between first position 408 and second position 410, as described herein (e.g., "bobbing" up and down to attract player attention). By the attract mode including movement of adjustable gaming device 400 between first position 408 and the second position 410, players are also made aware of the capability of adjustable gaming device 400 to move between first position 408 and second position 410 as desired by the player. Otherwise, for example, a player may consider playing or play at adjustable gaming device 400 without knowing about the option to adjust adjustable gaming device 400 between first position 408 and second position 410 (e.g., based on their preferences).

In some embodiments, the attract mode may also include display of certain messages and/or other displayed features (e.g., flashing lights) to attract player attention. In some embodiments, the attract mode may include display of a message regarding how recently adjustable gaming device 400 was cleaned (e.g., to notify potential players of the cleanliness of adjustable gaming device 400 and/or communicate the option for players to manually cause the cleaning apparatus to be activated). In some embodiments, adjustable gaming device 400 may vibrate when in the attract mode (e.g., or in response to another trigger condition).

In some embodiments, a plurality of adjustable gaming devices 400 may be controlled (e.g., by a device in communication with the adjustable gaming devices) to be in a synchronized attract mode. For example, a bank of adjustable gaming devices 400 may move between the first and second positions such that the bank of adjustable gaming devices 400 are at substantially the same position as they move between first position 408 and second position 410. In some embodiments, adjustable gaming devices 400 may move between first position 408 and second position 410 in a staggered manner (e.g., to give an appearance of adjustable gaming devices 400 "doing the wave" similar to a crowd at an event).

Further, one or more adjustable gaming devices 400 may be caused to be in a "celebration" mode. In some embodiments, the celebration mode is similar to the attract mode as described herein (e.g., movement of one or more adjustable gaming devices 400 between first position 408 and second position 410, flashing lights, certain messages being displayed, vibration of the one or more adjustable gaming devices 400 etc.). For example, in response to a jackpot win or other big win on a casino floor at or near one or more adjustable gaming devices 400, the one or more adjustable gaming devices 400 may enter the celebration mode to communicate to other players on the casino floor of the win (e.g., or other trigger event) and attract attention.

Figure 5:
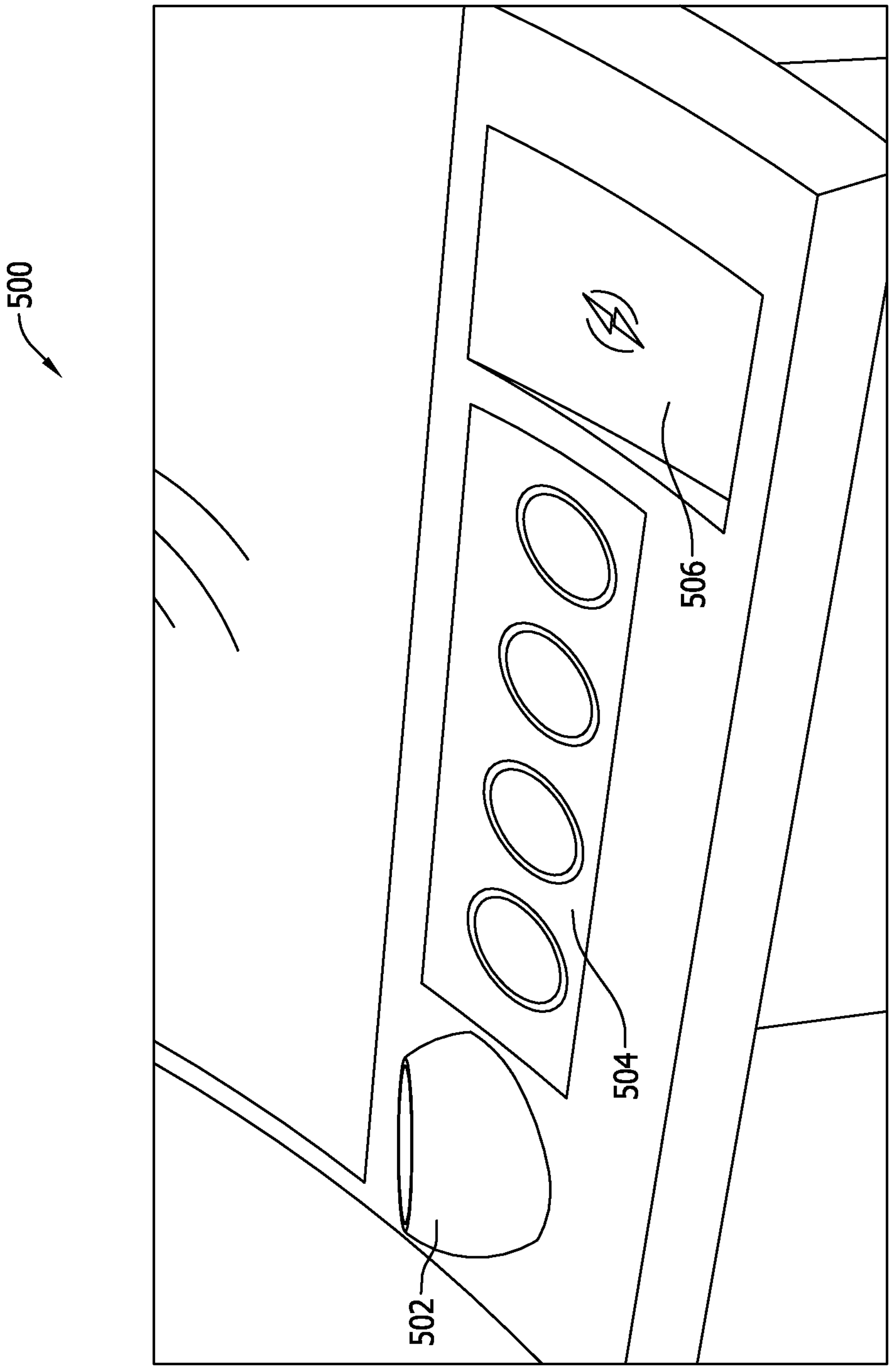
FIG. 5 illustrates a portion of the adjustable gaming device shown in FIG. 4.

FIG. 5 illustrates a portion 500 of adjustable gaming device 400 including a cupholder 502 (e.g., or other peripheral component), a button deck 504 (e.g., button deck 120, including virtual and/or mechanical buttons), and a wireless charging device 506 (e.g., for wireless charging and/or wireless operations as described herein). In some embodiments, other peripheral devices coupled to adjustable gaming device 400 are envisioned. FIG. 6 illustrates a side view of a portion 600 of adjustable gaming device 400. In the example embodiment, cupholder 502 is adjustable between a first position 602 and a second position 604. In the example of cupholder 502, the first position 602, second position 604, and transitions 606 therebetween, are configured to keep cupholder 502 (e.g., and a drink 608 therein) level regardless of position to avoid spills. In some embodiments, movement of cupholder 502 is controlled by a motor (e.g., in response to player input at adjustable gaming device 400, such as a button press) In some embodiments, movement of cupholder 502 is controlled manually by a user (e.g., a player, technician, etc.) at adjustable gaming device 400. In some embodiments, cupholder 502 does not move independently of display device 402 (e.g., and only moves with display device 402 when display device 402 moves between first position 408 and second position 410).

For example, cupholder 502 may be rotatable such that cupholder 502 remains level based on a current position (e.g., angle) of adjustable gaming device 400. In some embodiments, a screw may be positioned at the bottom of cupholder 502 and configured rotate cupholder 502 based on the current position of adjustable gaming device 400. For instance, when adjustable gaming device 400 is in first position 408, the screw may control the cupholder to be in a "lower" position (e.g., second position 604) while when adjustable gaming device 400 is in second position 410 the screw may control cupholder 502 to be in an "upper" position (e.g., first position 602). In some embodiments, cupholder 502 may be configured to move up and down adjustable gaming device 400, as shown in FIG. 6, while in some embodiments the cupholder may be configured to rotate in place in order to remain level.

One or more sensors may be utilized to determine a current position of adjustable gaming device 400 and a current position of cupholder 502. For example, a current position of adjustable gaming device 400 may be identified and a desired position of cupholder 502 may be determined based on the current position of adjustable gaming device 400 (e.g., in real time). For example, a lookup table stored in memory may be utilized to determine a desired position of cupholder 502 based on a current position of adjustable gaming device 400. Cupholder 502 may then be controlled (e.g., by one or more processors) to move to the desired position. Notably, the timeliness with which cupholder 502 moves is important in order to, for example, keep a drink level as adjustable gaming device 400 moves.

In some embodiments, means in addition to or alternatively from a screw may be utilized to control a position of cupholder 502. For example, in some embodiments cupholder 502 may rest on a spring-loaded ball and/or a user of adjustable gaming device 400 may be able to rotate/move cupholder 502 and/or "lock" cupholder 502 in place (e.g., by pressing a button) once cupholder 502 is in the desired position. In some embodiments, a gyroscope or similar device in communication with one or more processors may be utilized to identify a current position of cupholder 502.

In some embodiments, cupholder 502 may also include a sensor (e.g., an optical sensor) utilized to identify when an object is positioned in cupholder 502. For example, in some embodiments an identifier may be included on adjustable gaming device 400 (e.g., a designated light) to indicate whether an object is included in cupholder 502 or not. In some embodiments, whether or not an object is in cupholder 502 may be communicated to another device (e.g., a backend server). Thus, based on the identifier and/or communication to another device, casino floor staff, as an example, can easily identify when objects should be removed from cupholder 502 (e.g., no game is being played on adjustable gaming device 400 but an object remains in cupholder 502).

Figure 7:
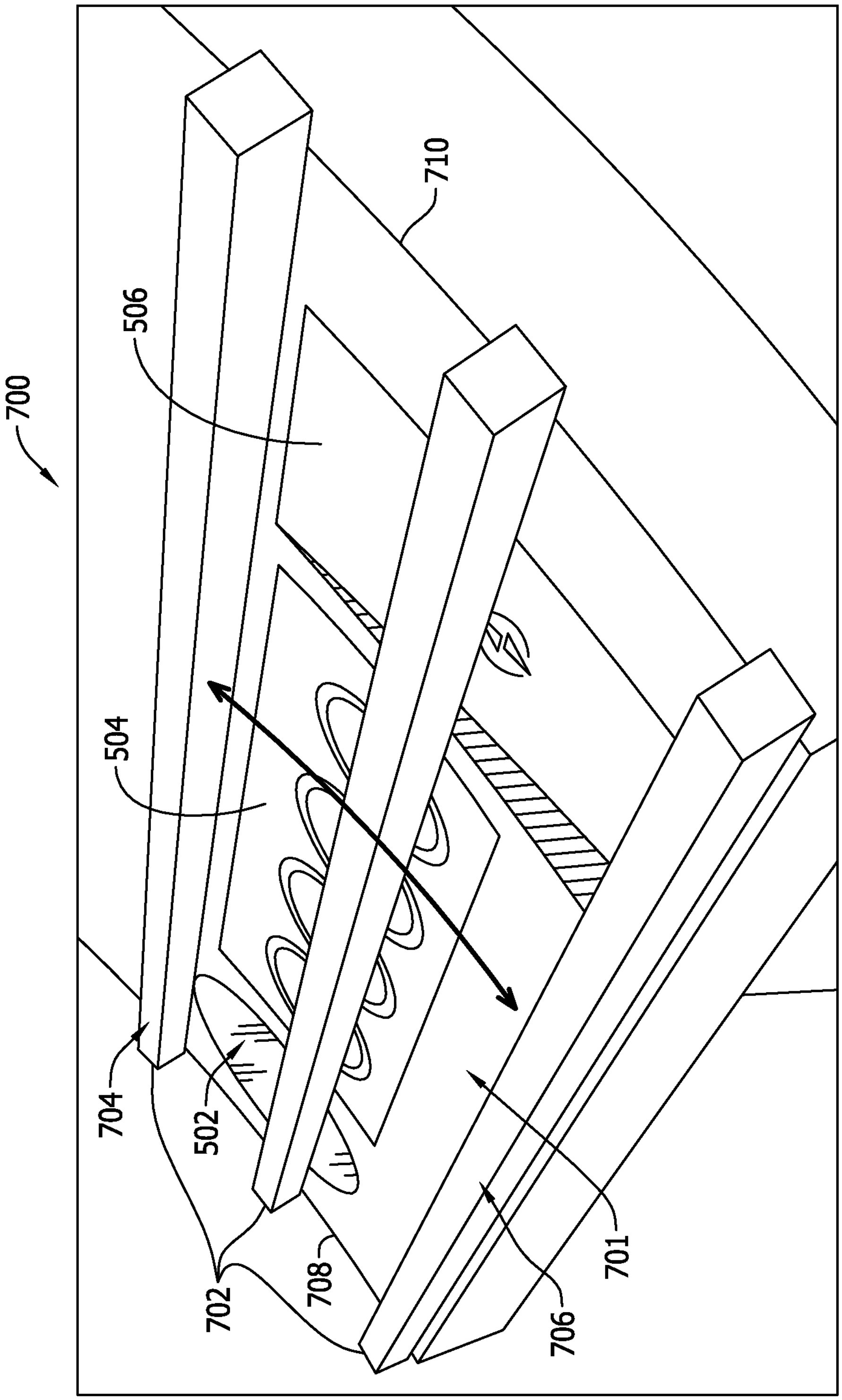
FIG. 7 illustrates a perspective view of a portion of the adjustable gaming device shown in FIG. 4.

FIG. 7 illustrates a perspective view of a portion 700 of adjustable gaming device 400. In the example shown in FIG. 7, adjustable gaming device 400 includes a disinfectant sprayer and/or ultraviolet (UV) light equipped cleaning apparatus 702 configured to travel between a first position 704 and a second position 706 (e.g., across button deck 504 and/or other components on an interface 701, such as wireless charging device 506) for cleaning before and after player engagement. For example, cleaning apparatus 702 may automatically clean when adjustable gaming device 400 detects that a gaming session has ended or begun. In some embodiments, cleaning apparatus may be located inside of adjustable gaming device 400 (e.g., to clean button deck 504 from underneath via UV light).

In some embodiments cleaning apparatus 702 may be activated based on an input from a user of adjustable gaming device 400 (e.g., a player, a technician, etc.). In other words, a player at adjustable gaming device 400 may be able to cause cleaning by apparatus 702 (e.g., via player input at adjustable gaming device 400, such as a button press). For example, a button (e.g., virtual or physical) may be provided on adjustable gaming device 400 such that selection of the button causes cleaning apparatus 702 to activate and clean button deck 504 (e.g., or other aspect of the adjustable gaming device).

In some embodiments, activation may be controlled based on an input at a device in communication with adjustable gaming device 400 such as a backend server, another gaming device, or a mobile device. For instance, a backend server or other gaming device may control cleaning of one or more adjustable gaming devices 400 (e.g., or other gaming devices) at predetermined times (e.g., based on a stored schedule) or at other stored or manually-selected times (e.g., before/after an event such as a tournament, at certain busy or slow times on a casino floor, etc.).

As noted above, in some embodiments cleaning apparatus 702 may be activated based on an input at a mobile device (e.g., in communication with adjustable gaming device 400 and associated with a player). For example, during play at adjustable gaming device 400 the player may select a button displayed at their mobile device (e.g., at a GUI caused to be displayed at the mobile device by adjustable gaming device 400 or backend server) that causes adjustable gaming device 400 to be activated (e.g., if button deck 504 appears dirty, in response to a spill, desired periodic cleaning, or any other reason). In some embodiments, a threshold amount of time may be required to pass (e.g., as tracked by adjustable gaming device 400 or a backend server) in between manual activations of cleaning apparatus 702 (e.g., to prevent repeated activation of cleaning apparatus 702).

In some embodiments, a notification may be presented to a player at adjustable gaming device 400 when cleaning apparatus 702 is going to be activated. For example, a notification may appear on adjustable gaming device 400 or a mobile device of the player a predetermined amount of time before cleaning will occur (e.g., to give the player to, if desired, end the gaming session and begin play on another machine). In some embodiments, the player may be provided with an option to provide an input to bypass the cleaning (e.g., to prevent interruption of their gaming session). In some embodiments, only certain players are provided the option to bypass cleaning (e.g., players of a certain loyalty tier).

Figure 8:
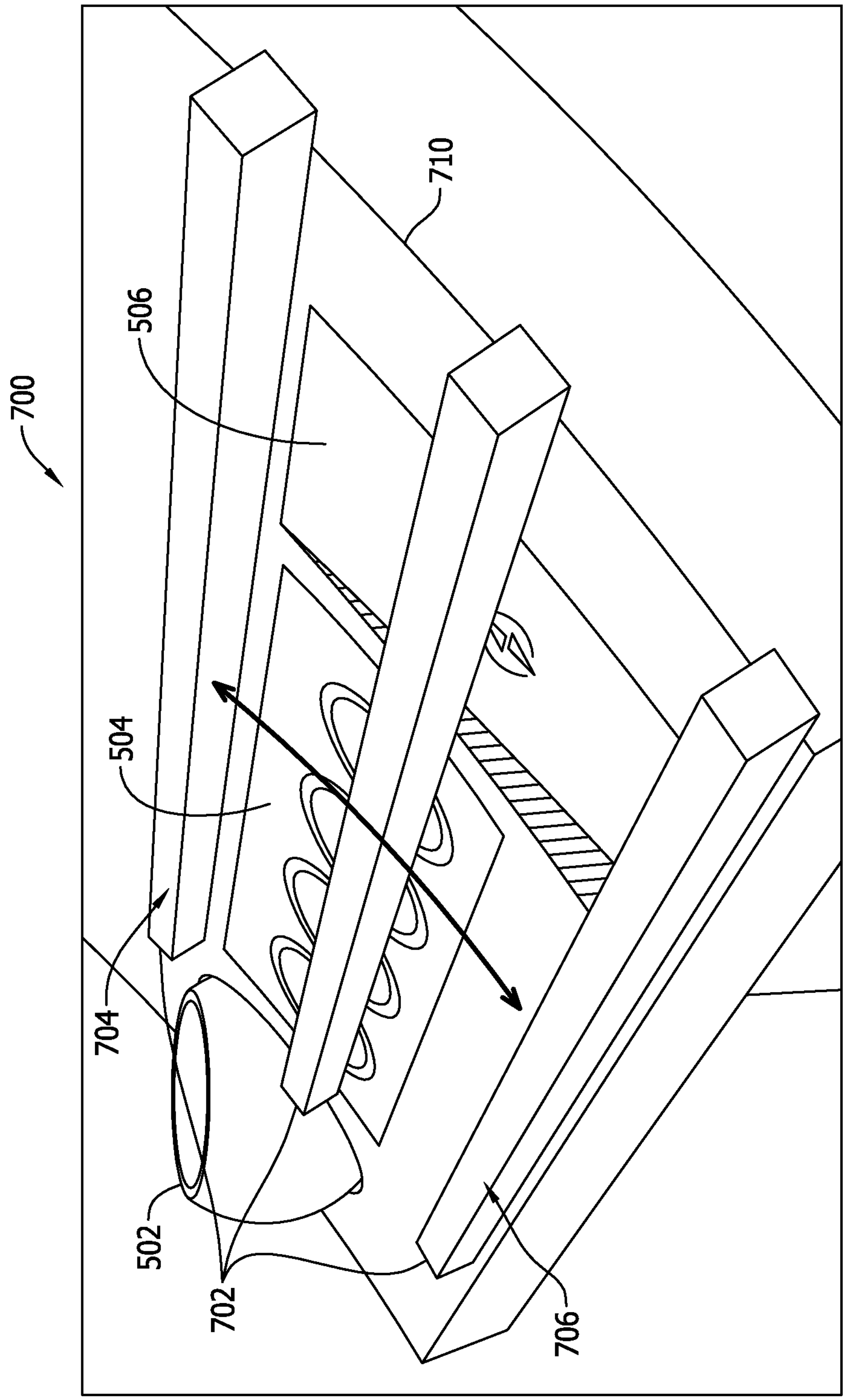
FIG. 8 illustrates an embodiment of the portion of the adjustable gaming device shown in FIG. 7.

FIG. 8 illustrates an embodiment 800 of portion 700 of the adjustable gaming device 400. For example, in FIG. 7, cupholder 502 may be positioned substantially within adjustable gaming device 400 such that cupholder 502 does not extend above a height of button deck 504. Accordingly, cleaning apparatus 702 may include a track on a left edge 708 of interface 701 and a right edge 710 of interface 701 so that cleaning apparatus 702, when activated, cleans all of interface 701.

In the example shown in FIG. 8, cupholder 502 extends upward (e.g., above a height of button deck 504). Accordingly, cleaning apparatus 702 extends across button deck 504 and wireless charging device 506 and includes one track at right edge 710 (e.g., because cleaning apparatus 702 would contact cupholder 502 if cleaning apparatus 702 extended from left edge 708 to right edge 710). In some embodiments, cleaning apparatus 702 may cover more or less portions of adjustable gaming device 400 than shown in FIGS. 7 and 8 (e.g., in some embodiments cleaning apparatus 702 may not extend over wireless charging device 506 in order to prevent, as an example, inadvertent cleaning of a player device located proximate wireless charging device 506.

Figure 9:
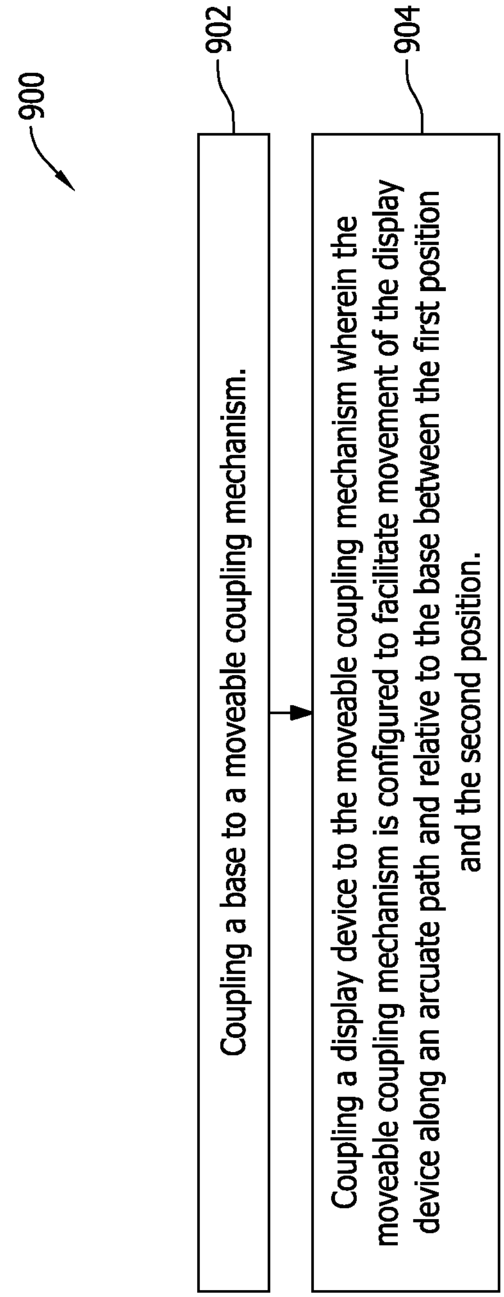
FIG. 9 illustrates a method for configuring the adjustable gaming device shown in FIG. 4.

FIG. 9 illustrates a method 900 for configuring the adjustable gaming device 400. In the example embodiment, method 900 is a method for configuring a display device (e.g., 402) of an electronic gaming device (e.g., 400) to be moveable between a first position (e.g., 408) and a second position (e.g., 410). Further, in the example embodiment method 900 includes coupling 902 a base (e.g., 406) to a moveable coupling mechanism. The example embodiment of method 900 also includes coupling 904 the display device to the moveable coupling mechanism wherein the moveable coupling mechanism is configured to facilitate movement of the display device along an arcuate path and relative to the base between the first position and the second position, and wherein in the first position the display device is held in an upright position and in the second position the display device is held in a lowered position.

In some embodiments of method 900, the display device is a curved display configured to display an electronic game wherein as the display device moves, the display device moves along the arcuate path moving a bottom edge of the display device away from the base and towards a player.

While the disclosure has been described with respect to the figures, it will be appreciated that many modifications and changes may be made by those skilled in the art without departing from the spirit of the disclosure. Any variation and derivation from the above description and figures are included in the scope of the present disclosure as defined by the claims.

What is claimed is:

1. An electronic gaming device comprising:
- a display device comprising a self-leveling peripheral component;
- a base; and
- a moveable coupling mechanism configured to couple the display device to the base and facilitate movement of the display device along an arcuate path and relative to the base between a first position and a second position, wherein in the first position the display device is held in an upright position and in the second position the display device is held in a lowered position, and wherein the self-leveling peripheral component is configured to remain level by transitioning between a first vertical position and a second vertical position on the display device as the display device moves along the arcuate path.

2. The electronic gaming device of claim 1, wherein the display device comprises a top edge and a bottom edge, and wherein in the first position the bottom edge is proximate to the base and wherein in the second position the bottom edge is positioned away from the base.

3. The electronic gaming device of claim 2, wherein in the upright position the top edge is higher than the top edge in the lowered position, wherein a plurality of other positions are included between the first position and the second position, and wherein the display device is configured to be positioned at any of the plurality of other positions.

4. The electronic gaming device of claim 1, wherein at least one processor causes the display device to move between the first position and the second position when the electronic gaming device is in an attract mode and no game is being played at the electronic gaming device.

5. The electronic gaming device of claim 1, wherein the display device comprises a curved display configured to display an electronic game, and wherein as the display device moves, the display device moves along the arcuate path moving a bottom edge of the display device away from the base.

6. The electronic gaming device of claim 5, wherein the display device comprises a button deck proximate to the bottom edge of the display device, and wherein when the display device moves away from the base, so does the button deck.

7. The electronic gaming device of claim 1, wherein the self-leveling peripheral component comprises a self-leveling drink holder.

8. The electronic gaming device of claim 1, wherein the self-leveling peripheral component comprises a wireless device.

9. The electronic gaming device of claim 6, wherein the button deck comprises at least one of a disinfectant or an ultraviolet (UV) light configured to clean the button deck.

10. An electronic gaming system comprising:

a display device comprising a self-leveling peripheral component;

a base; and a moveable coupling mechanism configured to couple the display device to the base and facilitate movement of the display device along an arcuate path and relative to the base between a first position and a second position, wherein in the first position the display device is held in an upright position and in the second position the display device is held in a lowered position, and wherein the self-leveling peripheral component is configured to remain level by transitioning between a first vertical position and a second vertical position on the display device as the display device moves along the arcuate path.

11. The electronic gaming system of claim 10, wherein the display device comprises a top edge and a bottom edge, and wherein in the first position the bottom edge is proximate to the base and wherein in the second position the bottom edge is positioned away from the base.

12. The electronic gaming system of claim 11, wherein in the upright position the top edge is higher than the top edge in the lowered position, wherein a plurality of other positions are included between the first position and the second position, and wherein the display device is configured to be positioned at any of the plurality of other positions.

13. The electronic gaming system of claim 10, wherein at least one processor causes the display device to move between the first position and the second position when the electronic gaming system is in an attract mode and no game is being played on the electronic gaming system.

14. The electronic gaming system of claim 10, wherein the display device comprises a curved display configured to display an electronic game, and wherein as the display device moves, the display device moves along the arcuate path moving a bottom edge of the display device away from the base.

15. The electronic gaming system of claim 14, wherein the display device comprises a button deck proximate to the bottom edge of the display device, and wherein when the display device moves away from the base, so does the button deck.

16. The electronic gaming system of claim 10, wherein the self-leveling peripheral component comprises a self-leveling drink holder.

17. The electronic gaming system of claim 10, wherein the self-leveling peripheral component comprises a wireless device.

18. The electronic gaming system of claim 15, wherein the button deck comprises at least one of a disinfectant or an ultraviolet (UV) light configured to clean the button deck.

19. A method for configuring a display device of an electronic gaming device to be moveable between a first position and a second position, the method comprising:

coupling a base to a moveable coupling mechanism; and coupling the display device to the moveable coupling mechanism, wherein the moveable coupling mechanism is configured to facilitate movement of the display device along an arcuate path and relative to the base between the first position and the second position, wherein in the first position the display device is held in an upright position and in the second position the display device is held in a lowered position, and wherein a self-leveling peripheral component of the electronic gaming device is configured to remain level by transitioning between a first vertical position and a second vertical position on the display device as the display device moves along the arcuate path.

20. The method of claim 19, wherein the display device comprises a curved display configured to display an electronic game, and wherein as the display device moves, the display device moves along the arcuate path moving a bottom edge of the display device away from the base and towards a player.

* * * * *